United States Patent
Davison

(10) Patent No.: US 7,722,530 B2
(45) Date of Patent: *May 25, 2010

(54) METHOD OF SECURING VERTEBRAE

(75) Inventor: Thomas W. Davison, North Attelboro, MA (US)

(73) Assignee: Zimmer Spine, Inc., Minneapolis, MN (US)

( * ) Notice: Subject to any disclaimer, the term of this patent is extended or adjusted under 35 U.S.C. 154(b) by 1817 days.

This patent is subject to a terminal disclaimer.

(21) Appl. No.: 10/686,154

(22) Filed: Oct. 15, 2003

(65) Prior Publication Data

US 2004/0236317 A1 Nov. 25, 2004

Related U.S. Application Data

(63) Continuation of application No. 10/280,489, filed on Oct. 25, 2002, now Pat. No. 7,056,321, which is a continuation-in-part of application No. 09/630,077, filed on Aug. 1, 2000, now Pat. No. 6,530,926.

(51) Int. Cl.
*A61B 1/00* (2006.01)
*A61M 29/00* (2006.01)
(52) U.S. Cl. ................................. 600/102; 606/130
(58) Field of Classification Search .............. 600/102, 600/114, 201, 203, 204; 606/198, 130; 604/364
See application file for complete search history.

(56) References Cited

U.S. PATENT DOCUMENTS

| 465,161 | A | 12/1891 | Chase |
|---|---|---|---|
| 2,235,979 | A | 3/1941 | Brown |
| 2,255,657 | A | 9/1941 | Freedman |
| 2,482,116 | A | 9/1949 | Lanahan |
| 2,575,253 | A | 11/1951 | Bicek |
| 2,594,086 | A | 4/1952 | Smith |
| 2,666,428 | A | 1/1954 | Glenner |
| 2,756,742 | A | 7/1956 | Barton |
| 2,829,649 | A | 4/1958 | Glenner |
| 2,886,004 | A | 5/1959 | Morrison |

(Continued)

FOREIGN PATENT DOCUMENTS

AU 13672/95 9/1995

(Continued)

OTHER PUBLICATIONS

Albee, An Excerpt from *Bone Graft Surgery in Disease, Injury and Deformity*, Preface: xi-x, 1940.

(Continued)

*Primary Examiner*—Vy Q Bui
(74) *Attorney, Agent, or Firm*—Crompton, Seager & Tufte, LLC

(57) ABSTRACT

A method of fixing vertebrae of a patient together at a surgical site includes the following steps: inserting a first cannula (10) into the body (130) of the patient; moving a first fastener (624) through the cannula (10) and securing the first fastener (624) to a first vertebrae (601); moving a second fastener (624) through the cannula (10) and securing the second fastener (624) to a second vertebrae (602); moving a first fixation element (650) through the cannula (10); and fixing the first fixation element (650) to the first and second fasteners (624).

35 Claims, 15 Drawing Sheets

U.S. PATENT DOCUMENTS

| | | |
|---|---|---|
| 3,044,461 A | 7/1962 | Murdock |
| 3,486,505 A | 12/1969 | Morrison |
| 3,570,498 A | 3/1971 | Weighton |
| 3,592,199 A | 7/1971 | Ostensen |
| 3,626,471 A | 12/1971 | Florin |
| 3,651,800 A | 3/1972 | Wilbanks |
| 3,788,318 A | 1/1974 | Kim et al. |
| 3,789,852 A | 2/1974 | Kim et al. |
| 3,875,595 A | 4/1975 | Froning |
| 3,941,127 A | 3/1976 | Froning |
| 3,964,480 A | 6/1976 | Froning |
| 4,013,078 A | 3/1977 | Feild |
| 4,049,000 A | 9/1977 | Williams |
| 4,232,660 A | 11/1980 | Coles |
| 4,254,763 A | 3/1981 | McCready et al. |
| 4,344,419 A | 8/1982 | Burgin |
| 4,350,151 A | 9/1982 | Scott |
| 4,421,108 A | 12/1983 | Cabrera et al. |
| 4,449,532 A | 5/1984 | Storz |
| 4,451,256 A | 5/1984 | Weikl et al. |
| 4,461,281 A | 7/1984 | Carson |
| 4,498,902 A | 2/1985 | Ash |
| 4,513,754 A | 4/1985 | Lee |
| 4,538,594 A | 9/1985 | Boebel et al. |
| 4,545,374 A | 10/1985 | Jacobson |
| 4,562,832 A | 1/1986 | Wilder et al. |
| 4,573,448 A | 3/1986 | Kambin |
| 4,573,454 A | 3/1986 | Hoffman |
| 4,586,491 A | 5/1986 | Carpenter |
| 4,601,713 A | 7/1986 | Fuqua |
| 4,617,929 A | 10/1986 | Gill |
| 4,638,799 A | 1/1987 | Moore |
| 4,655,216 A | 4/1987 | Tischer |
| 4,674,501 A | 6/1987 | Greenberg |
| 4,678,459 A | 7/1987 | Onik et al. |
| 4,696,544 A | 9/1987 | Costella |
| 4,700,694 A | 10/1987 | Shishido |
| 4,716,901 A | 1/1988 | Jackson et al. |
| 4,736,738 A | 4/1988 | Lipovsek et al. |
| 4,750,475 A | 6/1988 | Yoshihashi |
| 4,750,487 A | 6/1988 | Zanetti |
| 4,762,120 A | 8/1988 | Hussein |
| 4,790,297 A | 12/1988 | Luque |
| 4,819,620 A | 4/1989 | Okutsu |
| 4,834,757 A | 5/1989 | Brantigan |
| 4,837,995 A | 6/1989 | Omizono et al. |
| 4,850,342 A | 7/1989 | Hashiguchi et al. |
| 4,862,891 A | 9/1989 | Smith |
| 4,863,133 A | 9/1989 | Bonnell |
| 4,874,897 A | 10/1989 | Bickelhaupt et al. |
| 4,878,915 A | 11/1989 | Brantigan |
| 4,887,595 A | 12/1989 | Heinig et al. |
| 4,899,729 A | 2/1990 | Gill et al. |
| 4,904,261 A | 2/1990 | Dove et al. |
| 4,905,082 A | 2/1990 | Nishigaki et al. |
| 4,921,478 A | 5/1990 | Solano et al. |
| 4,947,896 A | 8/1990 | Bartlett |
| 4,972,827 A | 11/1990 | Kishi et al. |
| 4,984,564 A | 1/1991 | Yuen |
| 5,004,457 A | 4/1991 | Wyatt et al. |
| 5,015,247 A | 5/1991 | Michelson |
| 5,020,514 A | 6/1991 | Heckle |
| 5,025,778 A | 6/1991 | Silverstein et al. |
| 5,071,410 A | 12/1991 | Pazell |
| 5,108,420 A | 4/1992 | Marks |
| 5,112,354 A | 5/1992 | Sires |
| 5,125,396 A | 6/1992 | Ray |
| 5,131,382 A | 7/1992 | Meyer |
| 5,133,717 A | 7/1992 | Chopin |
| 5,139,487 A | 8/1992 | Baber |
| 5,139,499 A | 8/1992 | Small et al. |
| 5,139,511 A | 8/1992 | Gill et al. |
| 5,158,543 A | 10/1992 | Lazarus |
| 5,163,949 A | 11/1992 | Bonutti |
| 5,171,279 A | 12/1992 | Mathews |
| 5,190,561 A | 3/1993 | Graber |
| 5,195,507 A | 3/1993 | Bilweis |
| 5,195,541 A | 3/1993 | Obenchain |
| 5,197,971 A | 3/1993 | Bonutti |
| 5,201,729 A | 4/1993 | Hertzmann et al. |
| 5,224,680 A | 7/1993 | Greenstein et al. |
| 5,225,001 A | 7/1993 | Manni et al. |
| 5,242,444 A | 9/1993 | MacMillan |
| 5,279,564 A | 1/1994 | Taylor |
| 5,287,845 A | 2/1994 | Faul et al. |
| 5,295,994 A | 3/1994 | Bonutti |
| 5,312,417 A | 5/1994 | Wilk |
| 5,313,962 A | 5/1994 | Obenchain |
| 5,330,473 A | 7/1994 | Howland |
| 5,334,150 A | 8/1994 | Kaali |
| 5,339,802 A | 8/1994 | Cook |
| 5,339,803 A | 8/1994 | Mayzels et al. |
| 5,345,927 A | 9/1994 | Bonutti |
| 5,346,504 A | 9/1994 | Ortiz et al. |
| 5,353,784 A | 10/1994 | Nady-Mohamed |
| 5,354,302 A | 10/1994 | Ko |
| 5,357,983 A | 10/1994 | Mathews |
| 5,359,995 A | 11/1994 | Sewell, Jr. |
| 5,360,431 A | 11/1994 | Puno et al. |
| 5,364,395 A | 11/1994 | West, Jr. |
| 5,370,647 A * | 12/1994 | Graber et al. ................ 606/127 |
| 5,376,076 A | 12/1994 | Kaali |
| 5,380,291 A | 1/1995 | Kaali |
| 5,385,583 A | 1/1995 | Cotrel |
| 5,392,766 A | 2/1995 | Masterson et al. |
| 5,395,317 A | 3/1995 | Kambin |
| 5,396,880 A | 3/1995 | Kagan et al. |
| 5,437,637 A | 8/1995 | Lieber et al. |
| 5,437,671 A | 8/1995 | Lozier et al. |
| 5,437,672 A | 8/1995 | Alleyne |
| 5,439,449 A | 8/1995 | Mapes et al. |
| 5,439,464 A | 8/1995 | Shapiro |
| 5,441,041 A | 8/1995 | Sauer et al. |
| 5,441,042 A | 8/1995 | Putman |
| 5,443,058 A | 8/1995 | Ough |
| 5,443,467 A | 8/1995 | Biedermann et al. |
| 5,443,514 A | 8/1995 | Steffee |
| 5,445,142 A | 8/1995 | Hassler, Jr. |
| 5,454,365 A | 10/1995 | Bonutti |
| 5,470,333 A | 11/1995 | Ray |
| 5,472,426 A | 12/1995 | Bonati et al. |
| 5,480,440 A | 1/1996 | Kambin |
| 5,484,437 A | 1/1996 | Michelson |
| 5,487,744 A | 1/1996 | Howland |
| 5,489,307 A | 2/1996 | Kuslich et al. |
| 5,503,617 A | 4/1996 | Jako |
| 5,512,034 A | 4/1996 | Finn et al. |
| 5,520,607 A | 5/1996 | Frassica et al. |
| 5,534,009 A | 7/1996 | Lander |
| 5,549,595 A | 8/1996 | Freitas |
| 5,549,608 A | 8/1996 | Errico |
| 5,549,679 A | 8/1996 | Kuslich |
| 5,551,947 A | 9/1996 | Kaali |
| 5,554,157 A | 9/1996 | Errico et al. |
| 5,556,371 A | 9/1996 | Schulken et al. |
| 5,562,696 A | 10/1996 | Nobles et al. |
| 5,562,736 A | 10/1996 | Ray et al. |
| 5,569,205 A | 10/1996 | Hart et al. |
| 5,569,248 A | 10/1996 | Mathews |
| 5,571,072 A | 11/1996 | Kronner |
| 5,573,517 A | 11/1996 | Bonutti et al. |
| 5,575,754 A | 11/1996 | Konomura |
| 5,586,984 A | 12/1996 | Errico |
| 5,588,949 A | 12/1996 | Taylor et al. |

| Patent | Date | Inventor |
|---|---|---|
| 5,601,590 A | 2/1997 | Bonutti et al. |
| 5,601,690 A | 2/1997 | Gauld et al. |
| 5,603,688 A | 2/1997 | Upsher |
| 5,613,937 A | 3/1997 | Garrison et al. |
| 5,613,968 A | 3/1997 | Lin |
| 5,642,442 A | 6/1997 | Morton et al. |
| 5,643,282 A | 7/1997 | Kieturakis |
| 5,667,472 A | 9/1997 | Finn et al. |
| 5,667,473 A | 9/1997 | Finn et al. |
| 5,667,478 A | 9/1997 | McFarlin et al. |
| 5,667,520 A | 9/1997 | Bonutti |
| 5,672,176 A | 9/1997 | Biedermann et al. |
| 5,674,295 A | 10/1997 | Ray et al. |
| 5,681,319 A | 10/1997 | Biedermann et al. |
| 5,695,448 A | 12/1997 | Kimura et al. |
| 5,702,454 A | 12/1997 | Baumgartner |
| 5,707,359 A | 1/1998 | Bufalini |
| 5,716,356 A | 2/1998 | Biedermann et al. |
| 5,725,588 A | 3/1998 | Errico |
| 5,728,046 A | 3/1998 | Mayer et al. |
| 5,730,754 A | 3/1998 | Obenchain |
| 5,735,792 A | 4/1998 | Vanden Hoek et al. |
| 5,762,629 A | 6/1998 | Kambin |
| 5,772,661 A | 6/1998 | Michelson |
| 5,782,833 A | 7/1998 | Haider |
| 5,782,919 A | 7/1998 | Zdeblick et al. |
| 5,792,044 A | 8/1998 | Foley et al. |
| 5,795,289 A | 8/1998 | Wyttenbach |
| 5,797,911 A | 8/1998 | Sherman et al. |
| 5,810,809 A | 9/1998 | Rydell |
| 5,810,818 A | 9/1998 | Errico et al. |
| 5,813,978 A | 9/1998 | Jako |
| 5,814,084 A | 9/1998 | Grivas et al. |
| 5,823,947 A | 10/1998 | Yoon et al. |
| 5,824,093 A | 10/1998 | Ray et al. |
| 5,827,319 A | 10/1998 | Carlson et al. |
| 5,857,999 A | 1/1999 | Quick et al. |
| 5,863,293 A | 1/1999 | Richelsoph |
| 5,865,728 A | 2/1999 | Moll et al. |
| 5,865,802 A | 2/1999 | Yoon et al. |
| 5,868,745 A | 2/1999 | Alleyne |
| 5,873,878 A | 2/1999 | Harms et al. |
| 5,876,402 A | 3/1999 | Errico et al. |
| 5,879,389 A | 3/1999 | Koshino |
| 5,882,350 A | 3/1999 | Ralph et al. |
| 5,885,286 A | 3/1999 | Sherman et al. |
| 5,888,190 A | 3/1999 | Meyer et al. |
| 5,902,231 A | 5/1999 | Foley et al. |
| 5,910,142 A | 6/1999 | Tatar |
| 5,921,917 A | 7/1999 | Barthel et al. |
| 5,928,137 A | 7/1999 | Green |
| 5,928,232 A | 7/1999 | Howland et al. |
| 5,928,233 A | 7/1999 | Apfelbaum et al. |
| 5,954,635 A | 9/1999 | Foley et al. |
| 5,954,725 A | 9/1999 | Sherman et al. |
| 5,961,499 A | 10/1999 | Bonutti et al. |
| 5,961,517 A | 10/1999 | Biedermann et al. |
| 5,964,760 A | 10/1999 | Richelsoph |
| 5,984,928 A | 11/1999 | Hermann |
| 5,997,471 A | 12/1999 | Gumb et al. |
| 5,997,491 A | 12/1999 | Harris |
| 5,997,508 A | 12/1999 | Lunn et al. |
| 6,004,320 A | 12/1999 | Casscells et al. |
| 6,007,487 A | 12/1999 | Foley et al. |
| 6,007,533 A | 12/1999 | Casscells et al. |
| 6,010,503 A | 1/2000 | Richelsoph et al. |
| 6,022,376 A | 2/2000 | Assell et al. |
| 6,033,406 A | 3/2000 | Mathews |
| 6,050,997 A | 4/2000 | Mullane |
| 6,053,917 A | 4/2000 | Sherman et al. |
| 6,063,090 A | 5/2000 | Schlapfer |
| 6,074,380 A | 6/2000 | Byrne et al. |
| 6,074,391 A | 6/2000 | Metz-Stavenhagen et al. |
| 6,077,262 A | 6/2000 | Schapfer et al. |
| 6,086,588 A | 7/2000 | Ameil et al. |
| 6,090,111 A | 7/2000 | Nichols |
| 6,096,081 A | 8/2000 | Grivas et al. |
| 6,110,173 A | 8/2000 | Thomas, Jr. |
| 6,110,210 A | 8/2000 | Norton et al. |
| 6,113,601 A | 9/2000 | Tatar |
| 6,120,434 A | 9/2000 | Kimura et al. |
| 6,120,437 A | 9/2000 | Yoon et al. |
| 6,127,597 A | 10/2000 | Beyar et al. |
| 6,132,432 A | 10/2000 | Richelsoph |
| 6,132,465 A | 10/2000 | Ray et al. |
| 6,139,550 A | 10/2000 | Michelson |
| 6,142,931 A | 11/2000 | Kaji |
| 6,152,871 A | 11/2000 | Foley et al. |
| 6,162,170 A | 12/2000 | Foley et al. |
| 6,162,236 A | 12/2000 | Osada |
| 6,171,299 B1 | 1/2001 | Bonutti |
| 6,175,758 B1 | 1/2001 | Kambin |
| 6,176,823 B1 | 1/2001 | Foley et al. |
| 6,183,473 B1 | 2/2001 | Ashman |
| 6,187,000 B1 | 2/2001 | Davison et al. |
| 6,193,715 B1 | 2/2001 | Wrublewski et al. |
| 6,206,822 B1 | 3/2001 | Foley et al. |
| 6,206,922 B1 | 3/2001 | Zdeblick et al. |
| 6,214,001 B1 | 4/2001 | Casscells et al. |
| 6,217,509 B1 | 4/2001 | Foley et al. |
| 6,221,082 B1 | 4/2001 | Marino et al. |
| 6,224,545 B1 * | 5/2001 | Cocchia et al. ............. 600/233 |
| 6,248,105 B1 | 6/2001 | Schlapfer et al. |
| 6,258,024 B1 | 7/2001 | van Der Weegen |
| 6,261,586 B1 | 7/2001 | McKay |
| 6,267,765 B1 | 7/2001 | Taylor et al. |
| 6,270,498 B1 | 8/2001 | Michelson |
| 6,280,442 B1 | 8/2001 | Barker et al. |
| 6,293,949 B1 | 9/2001 | Justis et al. |
| 6,296,642 B1 | 10/2001 | Morrison et al. |
| 6,306,137 B2 | 10/2001 | Troxell |
| 6,306,170 B2 | 10/2001 | Ray |
| 6,309,391 B1 | 10/2001 | Crandall et al. |
| 6,312,443 B1 | 11/2001 | Stone |
| 6,325,812 B1 | 12/2001 | Dubrul et al. |
| 6,338,730 B1 | 1/2002 | Bonutti et al. |
| 6,355,038 B1 | 3/2002 | Pisharodi |
| 6,355,040 B1 | 3/2002 | Richelsoph et al. |
| 6,358,226 B1 | 3/2002 | Ryan |
| 6,358,266 B1 | 3/2002 | Bonutti |
| 6,361,488 B1 | 3/2002 | Davison et al. |
| 6,368,321 B1 | 4/2002 | Jackson |
| 6,371,968 B1 | 4/2002 | Kogasaka et al. |
| 6,383,195 B1 | 5/2002 | Richard |
| 6,387,130 B1 | 5/2002 | Stone et al. |
| 6,425,859 B1 | 7/2002 | Foley et al. |
| 6,440,133 B1 | 8/2002 | Beale et al. |
| 6,440,137 B1 | 8/2002 | Horvath et al. |
| 6,471,703 B1 | 10/2002 | Ashman |
| 6,478,797 B1 | 11/2002 | Paul |
| 6,482,207 B1 | 11/2002 | Errico |
| 6,485,491 B1 | 11/2002 | Farris et al. |
| 6,485,494 B1 | 11/2002 | Haider |
| 6,485,518 B1 | 11/2002 | Cornwall et al. |
| 6,494,893 B2 | 12/2002 | Dubrul et al. |
| 6,497,654 B1 | 12/2002 | Leonard et al. |
| 6,503,249 B1 | 1/2003 | Krause |
| 6,508,839 B1 | 1/2003 | Lambrecht et al. |
| 6,520,907 B1 | 2/2003 | Foley et al. |
| 6,520,926 B2 | 2/2003 | Hall |
| 6,524,320 B2 | 2/2003 | DiPoto |
| 6,530,880 B2 | 3/2003 | Pagliuca |
| 6,530,926 B1 | 3/2003 | Davison |
| 6,530,929 B1 | 3/2003 | Justis et al. |
| 6,530,930 B1 | 3/2003 | Marino et al. |
| 6,540,748 B2 | 4/2003 | Lombardo |

| | | | |
|---|---|---|---|
| 6,564,078 B1 | 5/2003 | Marino et al. | |
| 6,575,899 B1 * | 6/2003 | Foley et al. ................. 600/114 | |
| 6,602,291 B1 | 8/2003 | Ray et al. | |
| 6,610,094 B2 | 8/2003 | Husson | |
| 6,648,888 B1 | 11/2003 | Shluzas | |
| 6,652,553 B2 | 11/2003 | Davison et al. | |
| 6,679,833 B2 | 1/2004 | Smith et al. | |
| 6,719,794 B2 | 4/2004 | Gerber et al. | |
| 6,793,656 B1 | 9/2004 | Mathews | |
| 6,811,558 B2 | 11/2004 | Davison et al. | |
| 6,837,889 B2 | 1/2005 | Shluzas | |
| 6,887,248 B2 | 5/2005 | McKinley et al. | |
| 7,001,397 B2 | 2/2006 | Davison et al. | |
| 7,004,947 B2 | 2/2006 | Shluzas et al. | |
| 7,008,424 B2 | 3/2006 | Teitelbaum | |
| 7,066,937 B2 | 6/2006 | Shluzas | |
| 2001/0011170 A1 | 8/2001 | Davison et al. | |
| 2001/0049498 A1 | 12/2001 | Davison et al. | |
| 2002/0002360 A1 | 1/2002 | Orth et al. | |
| 2002/0022764 A1 | 2/2002 | Smith et al. | |
| 2002/0065560 A1 | 5/2002 | Varga et al. | |
| 2002/0143235 A1 | 10/2002 | Pagliuca | |
| 2003/0009130 A1 | 1/2003 | Stecker et al. | |
| 2003/0014068 A1 | 1/2003 | Bonutti et al. | |
| 2003/0040656 A1 | 2/2003 | Pagliuca et al. | |
| 2003/0073998 A1 | 4/2003 | Pagliuca et al. | |
| 2003/0139648 A1 | 7/2003 | Foley et al. | |
| 2003/0153927 A1 | 8/2003 | DiPoto et al. | |
| 2003/0191371 A1 | 10/2003 | Smith et al. | |
| 2003/0195405 A1 | 10/2003 | Marino et al. | |
| 2003/0195493 A1 | 10/2003 | Davison et al. | |
| 2003/0195549 A1 | 10/2003 | Davison et al. | |
| 2003/0195550 A1 | 10/2003 | Davison et al. | |
| 2003/0195551 A1 | 10/2003 | Davison et al. | |
| 2003/0199871 A1 | 10/2003 | Foley et al. | |
| 2003/0199885 A1 | 10/2003 | Davison et al. | |
| 2003/0208203 A1 | 11/2003 | Lim et al. | |
| 2003/0236529 A1 | 12/2003 | Shluzas et al. | |
| 2004/0059339 A1 | 3/2004 | Roehm, III et al. | |
| 2004/0078051 A1 | 4/2004 | Davison et al. | |
| 2004/0082960 A1 | 4/2004 | Davison | |
| 2004/0098012 A1 | 5/2004 | Davison et al. | |
| 2004/0116954 A1 | 6/2004 | Pagliuca et al. | |
| 2004/0133201 A1 | 7/2004 | Shluzas et al. | |
| 2004/0176763 A1 | 9/2004 | Foley et al. | |
| 2005/0021030 A1 | 1/2005 | Pagliuca et al. | |
| 2005/0033297 A1 | 2/2005 | Davison | |
| 2005/0043754 A1 | 2/2005 | Davison et al. | |
| 2005/0113833 A1 | 5/2005 | Davison | |
| 2006/0089662 A1 | 4/2006 | Davison et al. | |
| 2006/0264999 A1 | 11/2006 | Davison et al. | |
| 2006/0276821 A1 | 12/2006 | Davison et al. | |
| 2006/0276822 A1 | 12/2006 | Davison et al. | |
| 2006/0293678 A1 | 12/2006 | Davison et al. | |

FOREIGN PATENT DOCUMENTS

| | | |
|---|---|---|
| DE | 1566116 | 1/1970 |
| DE | 2222979 | 11/1973 |
| DE | 3108766 | 9/1982 |
| DE | 3936811 | 9/1990 |
| EP | 0303824 | 2/1989 |
| EP | 0 528 562 A2 | 2/1993 |
| EP | 0682918 | 11/1995 |
| EP | 0 807 415 A3 | 8/1998 |
| EP | 0 980 677 A1 | 2/2000 |
| EP | 1090595 | 4/2001 |
| EP | 1 305 077 A1 | 5/2003 |
| FR | 2 701 379 | 8/1994 |
| FR | 2714285 | 6/1995 |
| GB | 2234906 | 2/1991 |
| JP | 2000-83960 A2 | 3/2000 |
| JP | 2001-149376 A2 | 6/2001 |
| WO | WO 83/03189 | 9/1983 |
| WO | WO 91/06266 | 5/1991 |
| WO | WO 92/19146 | 11/1992 |
| WO | WO 92/21292 A2 | 2/1993 |
| WO | WO 93/14801 A1 | 8/1993 |
| WO | WO 93/15647 | 8/1993 |
| WO | WO 94/03114 A1 | 2/1994 |
| WO | WO 95/10218 A1 | 4/1995 |
| WO | WO 95/22285 | 8/1995 |
| WO | WO 95/32663 A1 | 12/1995 |
| WO | WO 98/27884 | 7/1998 |
| WO | WO 98/33462 | 8/1998 |
| WO | WO 00/18306 | 4/2000 |
| WO | WO 01/54560 A3 | 8/2001 |
| WO | WO 02/09801 A1 | 2/2002 |
| WO | WO 02/22030 | 3/2002 |
| WO | WO 02/078767 A2 | 10/2002 |
| WO | WO 03/007783 A2 | 1/2003 |

OTHER PUBLICATIONS

Caspar, "The Caspar Microsurgical Discectomy and Comparison with a Conventional Standard Lumbar Disc Procedure," Neurosurgery, 1 (28): 78-87, Jan. 1991.

Letter and Suggestion of Interference in U.S. Appl. No. 10/734,161, filed Oct. 25, 2006.

Response to Office Action mailed Jan. 3, 2006 in U.S. Appl. No. 10/734,161, filed Jul. 3, 2006.

Destandau, "A Special Device for Endoscopic Surgery of Lumbar Disc Herniation," Neurological Research, vol. 21: 39-42, Jan. 1999.

Ditsworth, "A New and Superior Technique for Removal of Herniated Lumbar Disc: Endoscope and Nucleotome Combination," The Joint Section on Spine and Peripheral Nerves, Abstract, Feb. 1995.

Ditsworth, "Comprehensive Percutaneous Endoscopic Spinal Surgery," The American Association of Neurological Surgeons, Abstract, 1995.

Ditsworth, "Endoscopic Transforaminal Lumbar Discectomy and Reconfiguration: A Posterolateral Approach Into the Spinal Canal," Surg. Neurol., 49: 588-598, 1998.

Endius™ presentation materials, "Spine Endoscopy System with FlexPosure," 2 pgs., 1999.

ENDIUS, Atavi Atraumatic Spine Fusion System Marketing Bulletin, "How Do I Decompress Using Atavi System?", Mar. 4, 2002.

ENDIUS, Atavi Atraumatic Spine Fusion System Marketing Bulletin, "Minimally Invasive Update on Danek," Apr. 12, 2002.

Foley et al., "Percutaneous Pedicle Screw Fixation of the Lumbar Spine," Neurosurg. Focus, 4 (10): 1-8, Apr. 2001.

Guiot et al., "A Minimally Invasive Technique for Decompression of the Lumbar Spine," 4 (27): 432-438, 2002.

Kambin, "Arthroscopic Microdiscectomy," The Adult Spine: Principles and Practice, 94: 2023-2036, 1997.

Kambin, "Arthroscopic Lumbar Interbody Fusion," Spine Care White AH, 77: 1055-1056, 1995.

Kambin, "Arthroscopic Lumbar Intervertebral Fusion," The Adult Spine, Principals and Practice, 95: 2037-2046, 1997.

Kambin, "Arthroscopic Techniques for Spinal Surgery," Operative Arthroscopy, Second Edition, 89: 1215-1225, 1996.

Kambin, "Diagnostic and Therapeutic Spinal Arthroscopy," Neurosurgery Clinics of North America, 1 (7): 65-76, 1996.

Kambin, "Endoscopic Laminotomy Procedures," On sale and in public use in the United States more than one year prior to Aug. 1, 2000.

Kambin, "Posterolateral Percutaneous Lumbar Interbody Fusion," Arthroscopic Microdiscectomy, Minimal Intervention in Spinal Surgery, 9: 117-121, 1991.

Kambin, "The Role of Minimally Invasive Surgery in Spinal Disorders," Advances in Operative Orthopaedics, vol. 3: 147-171, 1995.

Liu et al., "Posterior Fusion of the Subaxial Cervical Spine: Indications and Techniques," Neurosurgery Focus 4 (10): Article 7, Apr. 2001.

Leonard Medical Inc., Brochure Entitled, "Instruments for Less Invasive Surgery," 6 pgs., prior to Aug. 1, 2000.

Mathews, "Spinal Endoscopy Evolution, Applications & Foundations," 1-44, on or before Oct. 25, 2002.

MED™ presentation materials, "MicroEndoscopic Discectomy System," 33 pgs., 1997.

Medtronic Sofamor Danek, "An Evolution in Minimally Invasive Spine Surgery," METRx, MicroEndoscopic Discectomy, 6 pgs., 1999.

Medtronic Sofamor Danek, "METRx Microdiscectomy Surgical Technique," as described by Donald L. Hilton Jr., M.D., F.A.C.S. and Sylvain Palmer, F.A.C.S., 19 pgs., 2001.

Medtronic Sofamor Danek, "The Next Step in Minimally Invasive Discectomy Utilizing the Operating Microscope," 2 pgs., 2000.

Muskoskeletal Transplant Foundation presentation materials, "The MTF EndoDowel™" 2 pgs., Jun. 1996.

Muskoskeletal Transplant Foundation presentation materials: 1-16, Apr. 1996.

Request for Declaration of Interference filed in U.S. Appl. No. 10/734,161, filed Jan. 29, 2004.

Sofamor Danek brochure, "Laparoscopic Bone Dowel Instruments," 2 pgs., 1995.

Sofamor Danek brochure, "Micro-Endo Systems," 2 pgs., 1994.

Sofamor Danek presentation materials, "Laparoscopic Bone Dowel Surgical Technique," 17 pgs., 1995.

Stauber et al., "Pedicle Screw Placement with Intrasseous Endoscopy," SPINE, 1 (19): 57-61, 1994.

Synthes Spine, "Synthes Spine Top Loading System: Click X," Technique Guide, 2000.

U.S. Appl. No. 07/328,952, Material cancelled from Meyer Application. Mailed Mar. 27 1989, publicly available at least on Jul. 21, 1992.

Vich, "Anterior Cervical Interbody Fusion with Threaded Cylindrical Bone," J. Neurosurg, vol. 63: 750-753, 1985.

* cited by examiner

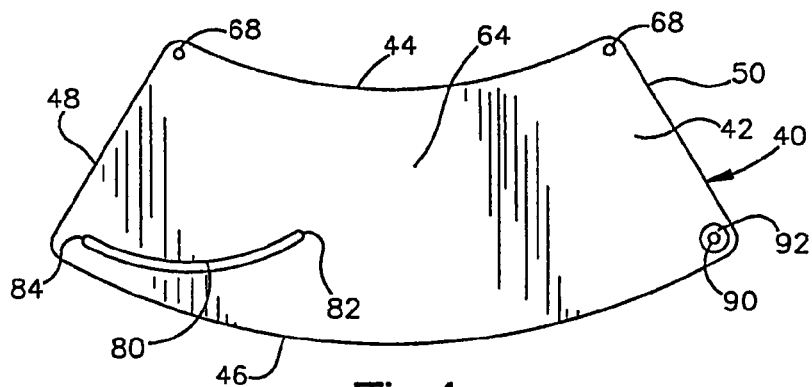
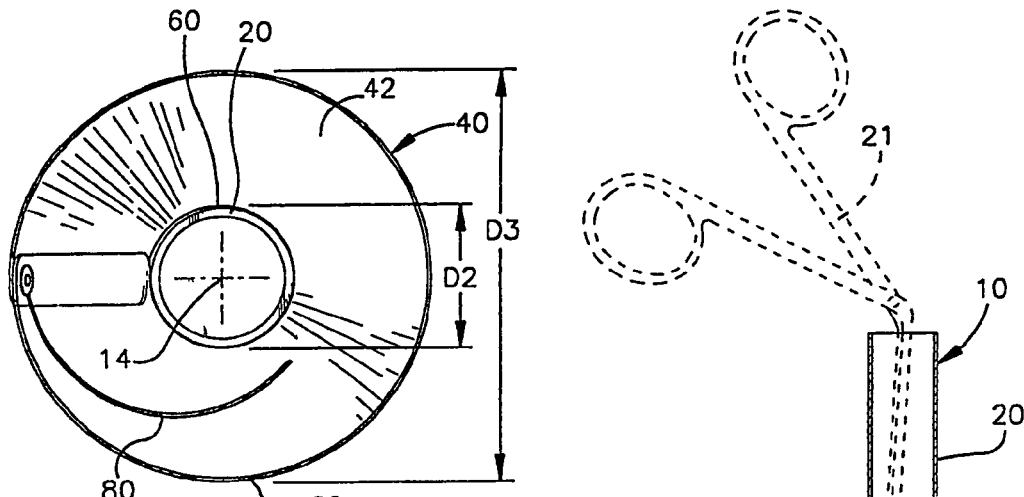
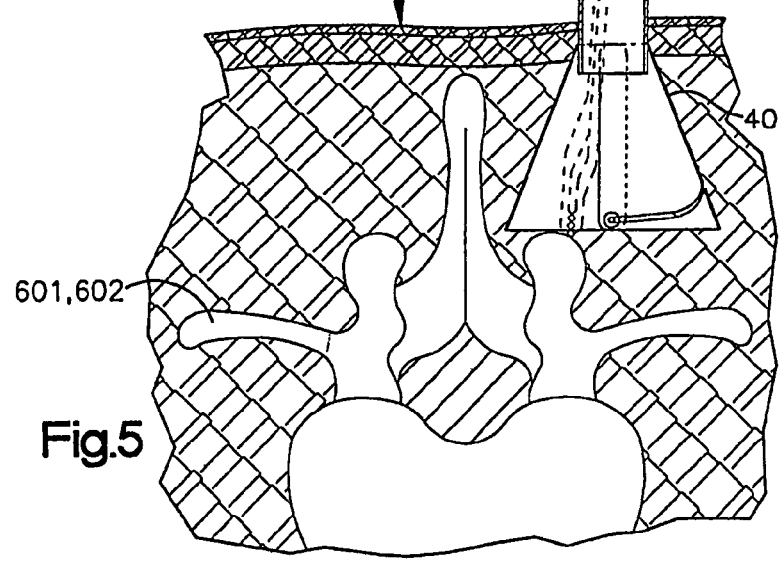

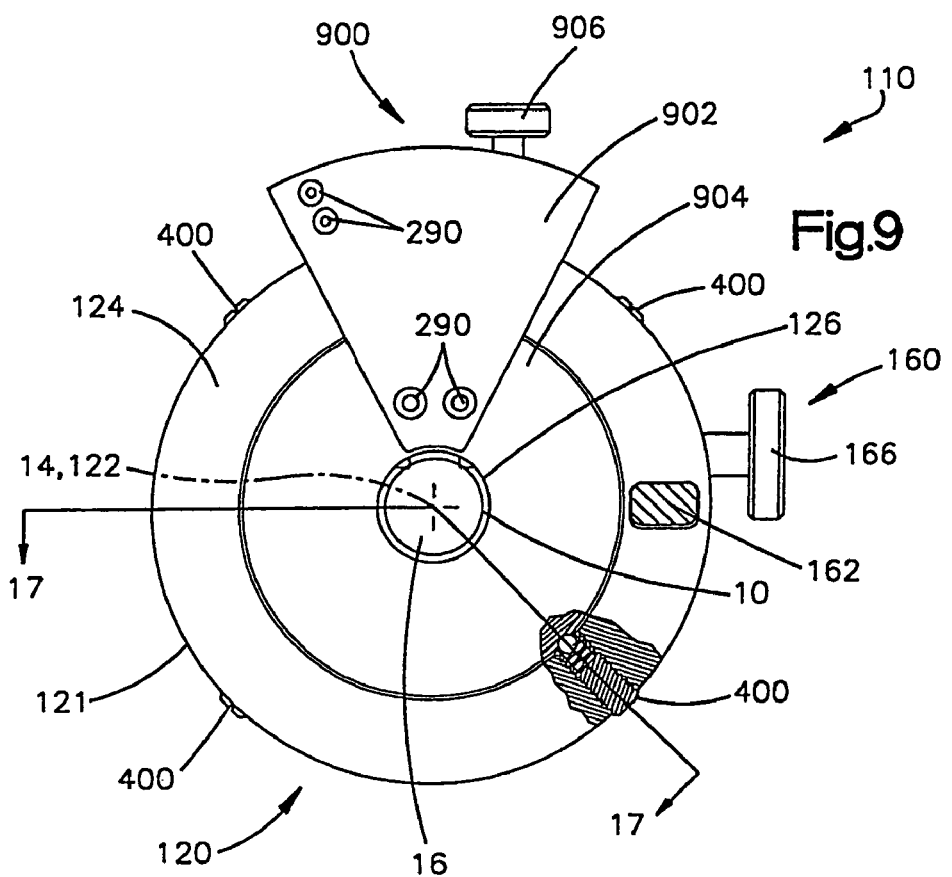
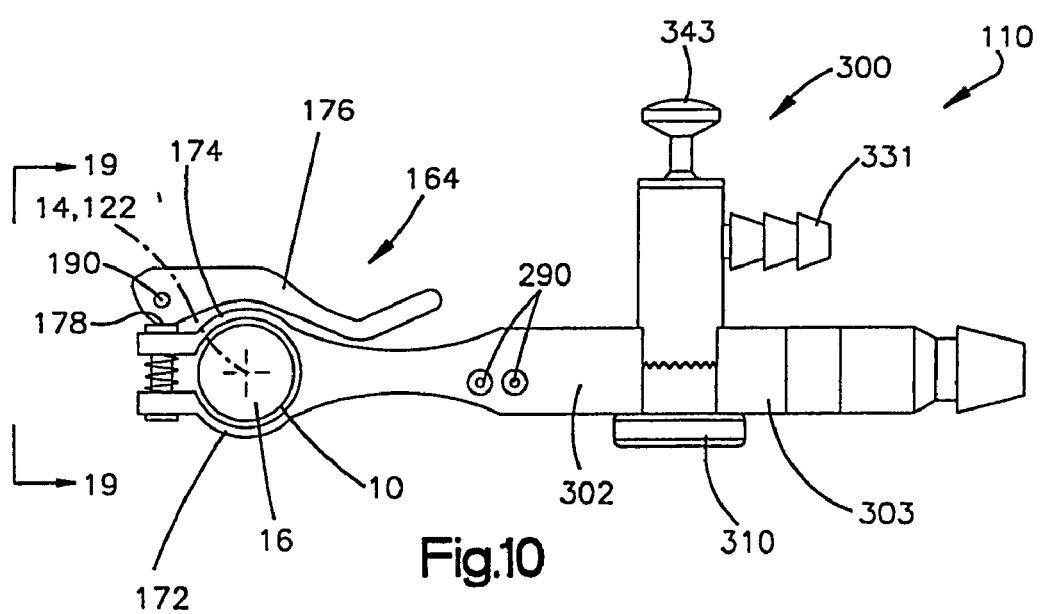

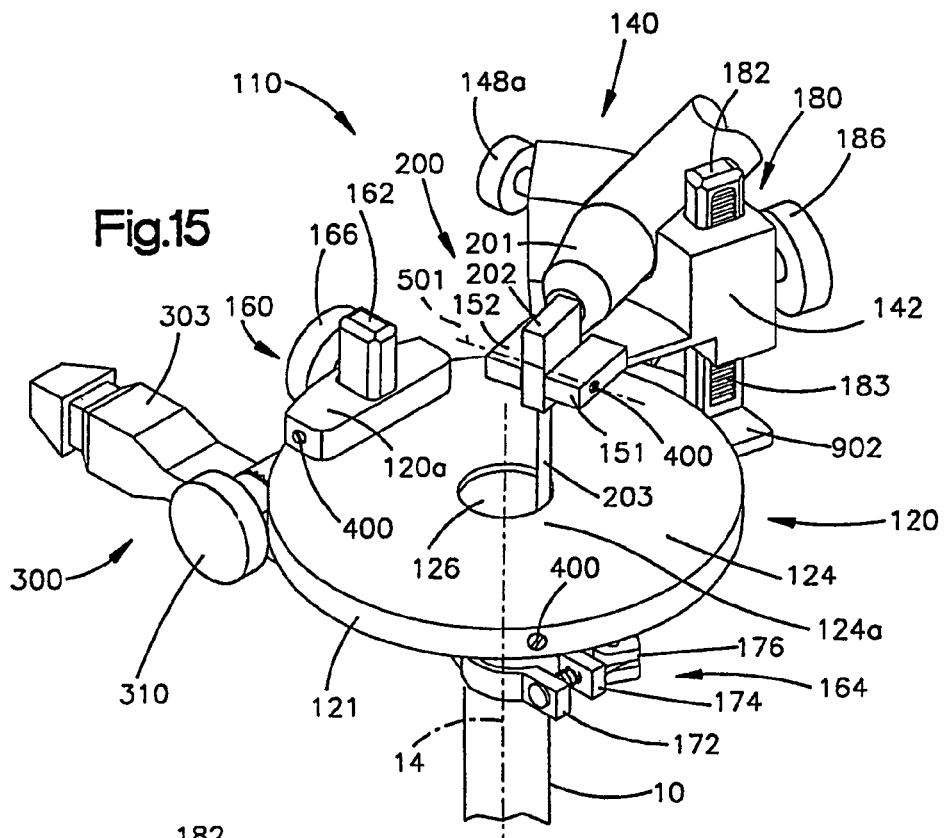
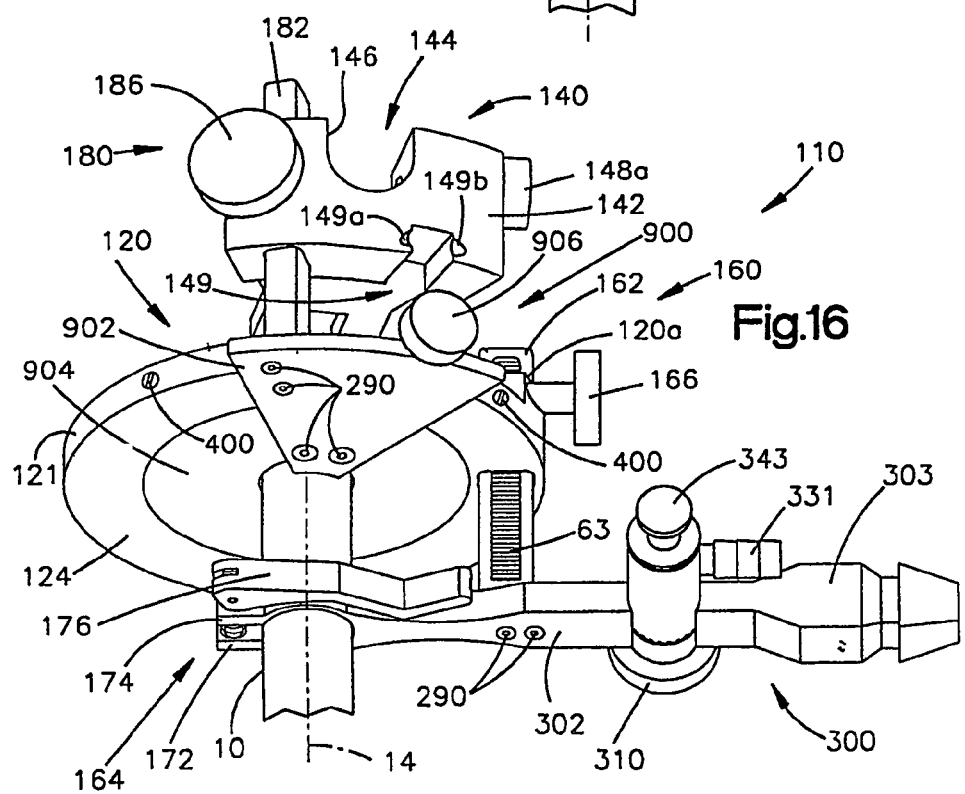

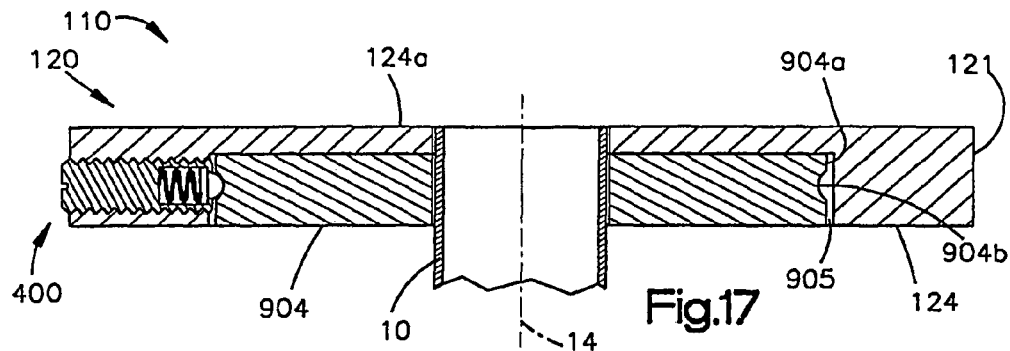
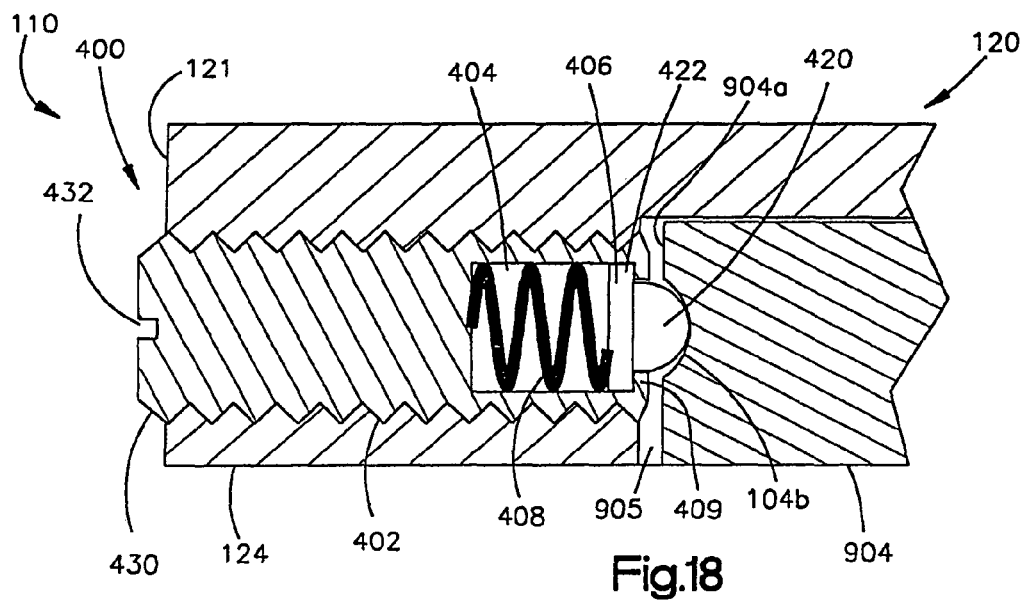
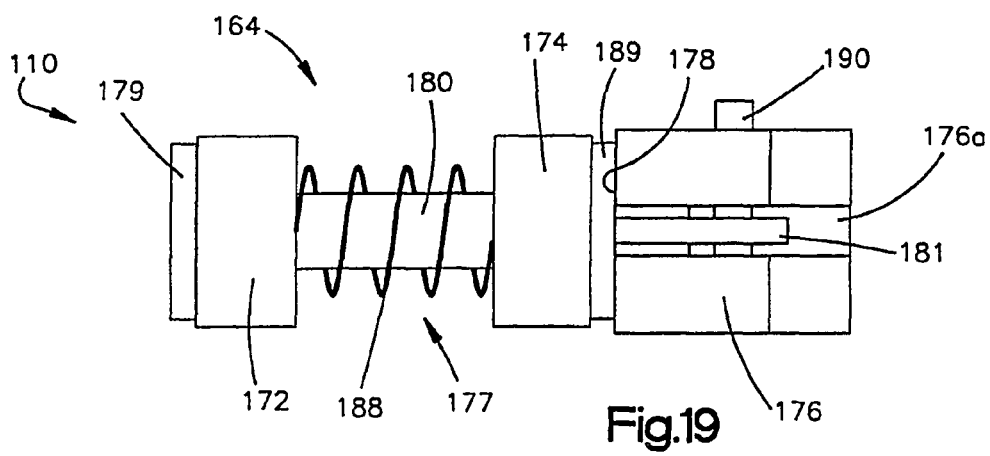

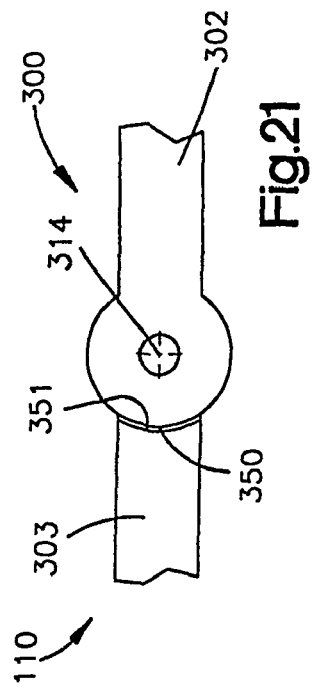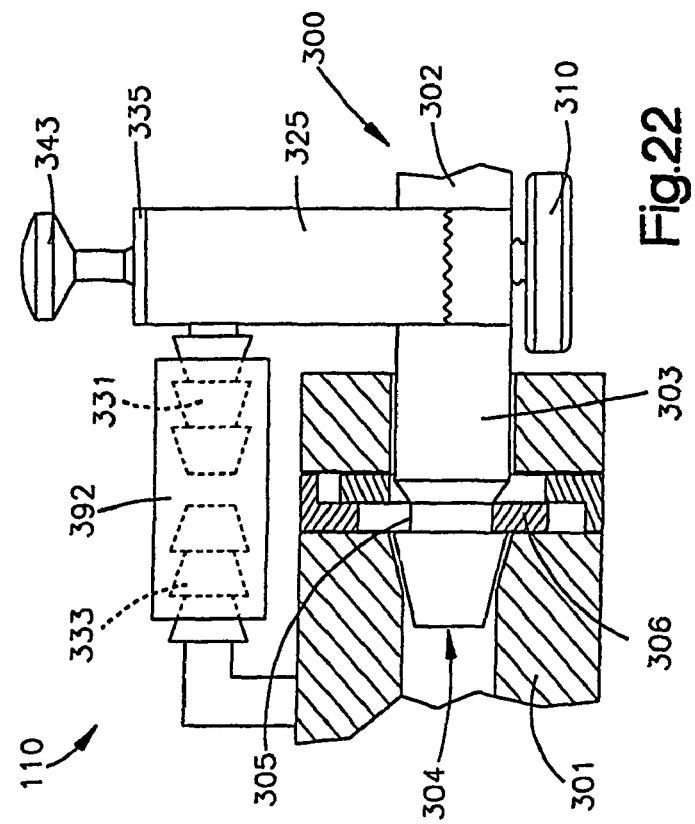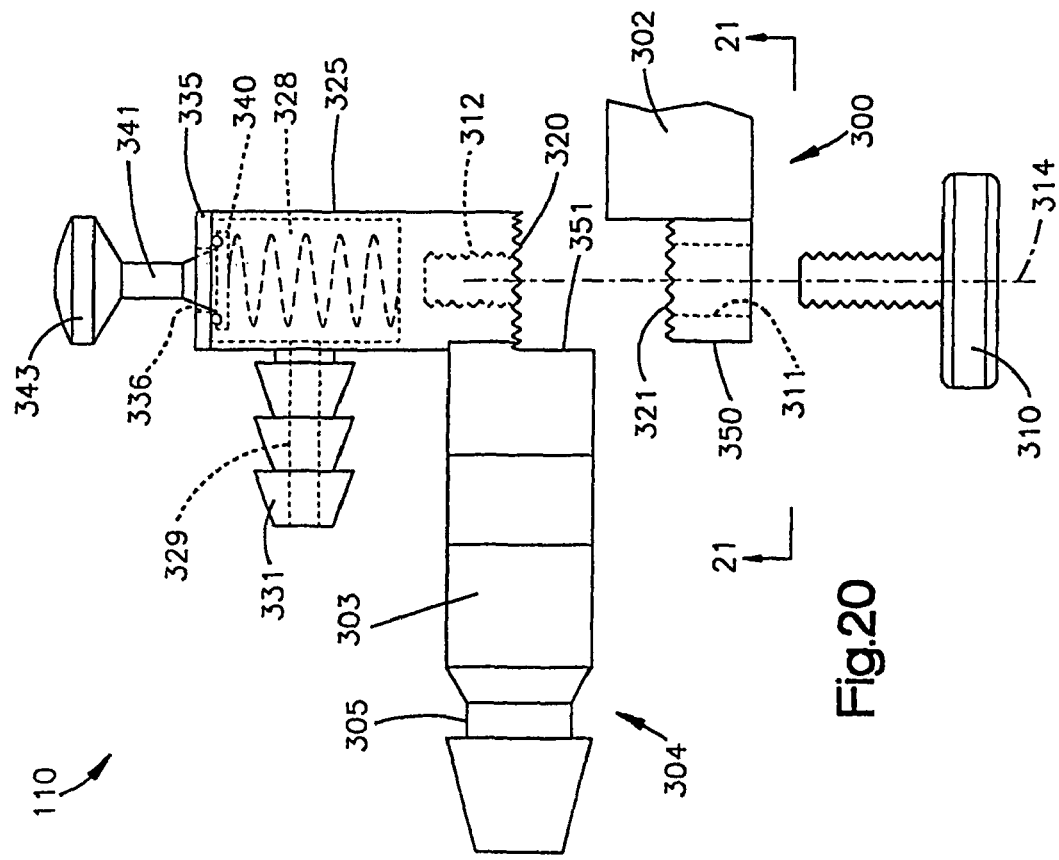

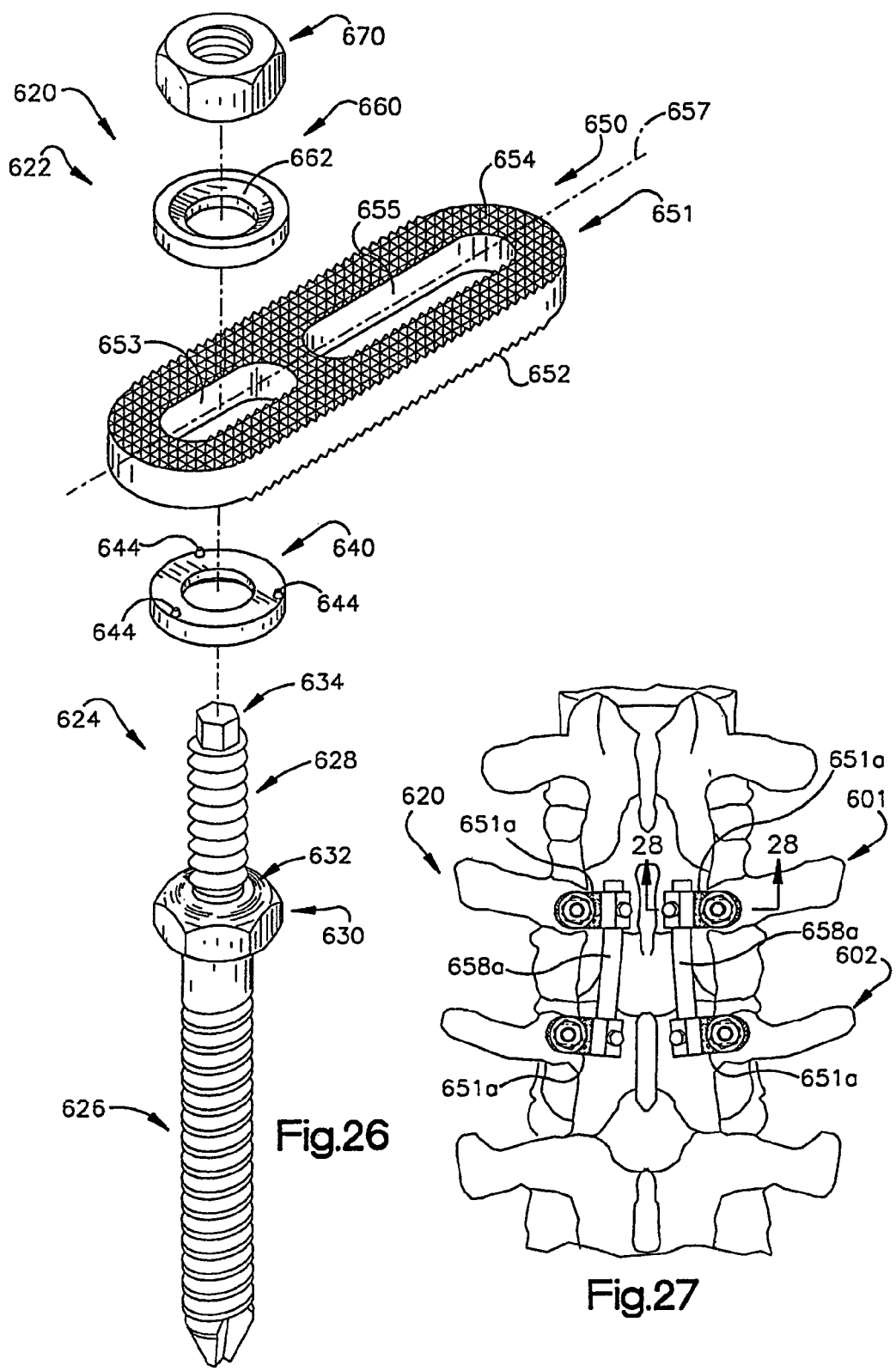

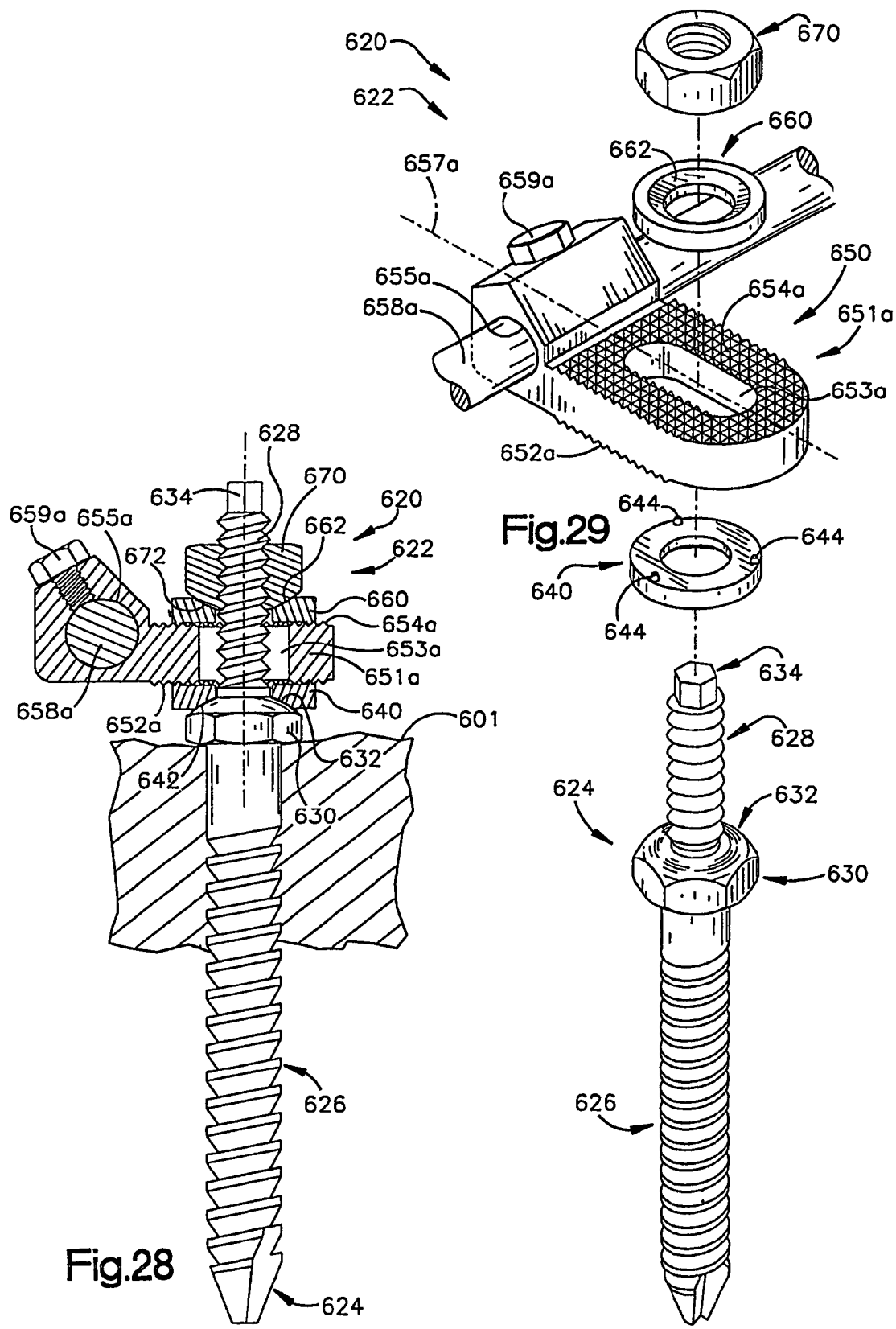

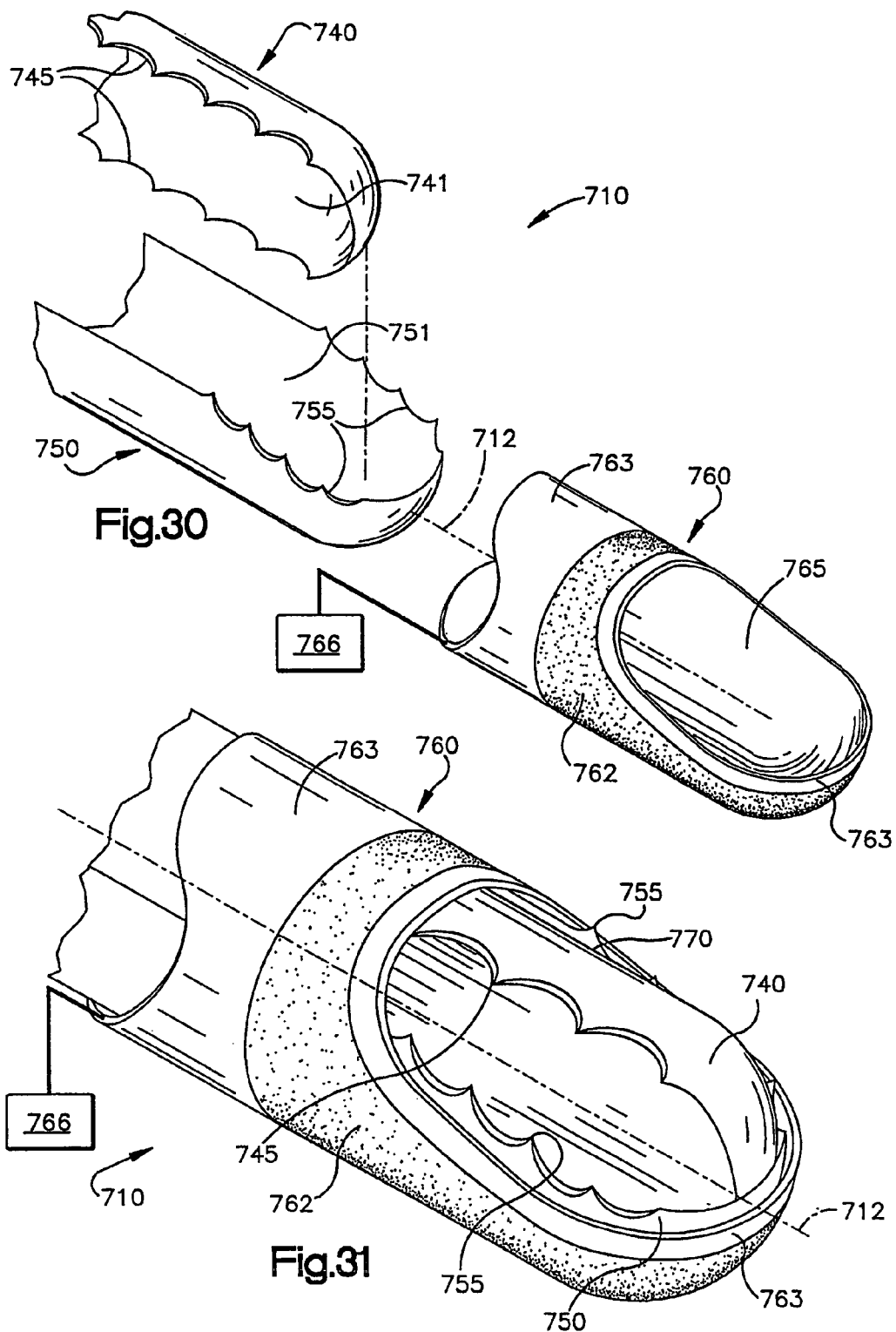

METHOD OF SECURING VERTEBRAE

RELATED APPLICATIONS

This application is a continuation of U.S. application Ser. No. 10/280,489, filed Oct. 25, 2002, now U.S. Pat. No. 7,056,321, which is a continuation-in-part of U.S. application Ser. No. 09/630,077, filed Aug. 1, 2000, now U.S. Pat. No. 6,530,926.

TECHNICAL FIELD

The present invention relates to a method of fixing vertebrae of a patient together at a surgical site.

BACKGROUND OF THE INVENTION

Percutaneous surgery is a procedure in which surgical instruments and an endoscope are inserted through a cannula into the body of a patient. A viewing element, typically a small video camera, is part of the endoscope and is connected to a monitor so that the surgeon may view the surgical site.

The cannula is a hollow tube that is inserted through an incision into the body of a patient so that a distal end of the cannula lies adjacent the surgical site. The instruments, usually one at a time, and the endoscope are inserted through the cannula. The cannula also allows the instruments and endoscope to be removed from the body and/or adjusted in the body during the surgery without trauma to the body.

A conventional apparatus for supporting the cannula and the endoscope allows a surgeon to manipulate the surgical instruments without also moving the endoscope. Also, a known support apparatus allows adjustment of the endoscope relative to the cannula for viewing different areas of the surgical site in the body.

While the above described apparatus enables many types of surgeries at small surgical sites, the fixing of vertebrae together has heretofore been conducted by a much more invasive open surgical method.

SUMMARY OF THE INVENTION

In accordance with the present invention, a method of fixing vertebrae of a patient together at a surgical site includes the following steps: inserting a first cannula into the body of the patent; moving a first fastener through the cannula and securing the first fastener to a first vertebrae; moving a second fastener through the cannula and securing the second fastener to a second vertebrae; moving a first fixation element through the cannula; and fixing the first fixation element to the first and second fasteners.

BRIEF DESCRIPTION OF THE DRAWINGS

The foregoing and other features of the present invention will become more apparent to one skilled in the art upon consideration of the following description of the invention and the accompanying drawings in which:

FIG. 3 is a schematic end view showing the cannula of FIG. 1 in the expanded position;

FIG. 4 is a rollout view of a part of the cannula of FIG. 1;

FIG. 5 is a schematic sectional view of the cannula of FIG. 1 during a surgical procedure.

FIG. 9 is a schematic view taken along line 9-9 in FIG. 6 showing part of the support apparatus of FIG. 6;

FIG. 10 is a schematic view taken along line 10-10 in FIG. 6 with parts removed;

FIG. 15 is a perspective view of the support apparatus of FIG. 6 looking at the support apparatus from an angle different than FIG. 13;

FIG. 16 is a perspective view of the support apparatus of FIG. 6 looking at the support apparatus from an angle different than FIGS. 14 and 15;

FIG. 17 is a sectional view taken approximately along line 17-17 of FIG. 9;

FIG. 18 is an enlarged view of a part of FIG. 17;

FIG. 19 is a schematic view taken along line 19-19 in FIG. 10 with parts removed;

FIG. 20 is a view further illustrating parts shown in FIG. 10;

FIG. 21 is a view taken approximately along line 21-21 of FIG. 20;

FIG. 22 is a schematic view showing the support apparatus with an associated known mechanical arm;

FIG. 26 is an exploded schematic view of part of the assembly of FIG. 24;

FIG. 27 is a schematic view of another fixation assembly attached to vertebrae of a patient;

FIG. 28 is a schematic view taken along line 28-28 of FIG. 27;

FIG. 29 is an exploded schematic view of part of the assembly of FIG. 27;

FIG. 30 is an exploded view of part of a cutting tool used with the claimed method; and FIG. 31 is an assembled view of part of the cutting tool of FIG. 30.

DESCRIPTION OF A PREFERRED EMBODIMENT

Figure 1:
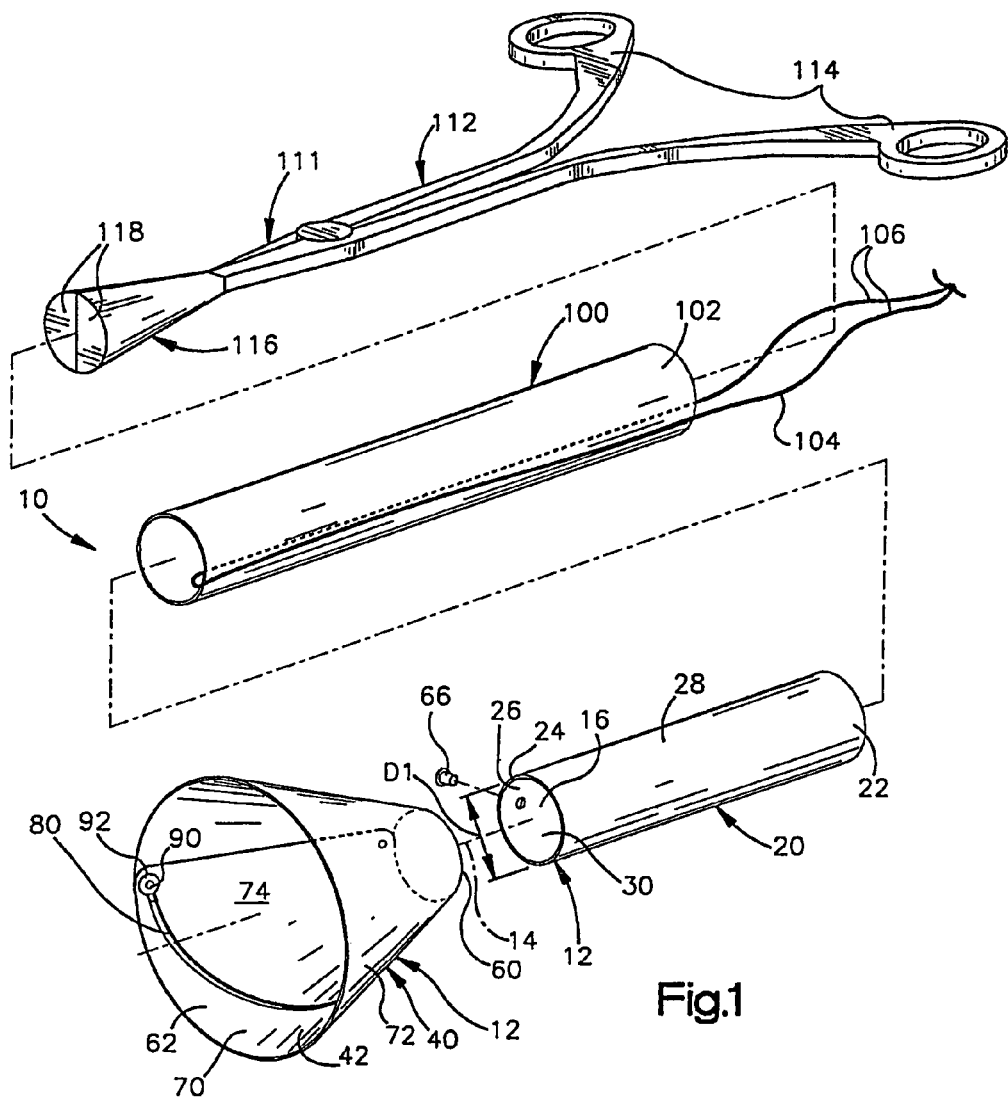
FIG. 1 is an exploded perspective view of a surgical cannula constructed for use with the present invention, the cannula being shown in an expanded condition.

The present invention is directed to a method for fixing the vertebrae of a patient at a surgical site.

The method involves the use of a cannula, an adjustable support for the cannula, and the inserting of surgical instruments, a viewing device, and a vertebral fixation assembly through the cannula to the surgical site.

FIGS. 1-5 illustrate one suitable cannula 10 constructed for use in a method in accordance with the present invention. The cannula 10 is a tubular structure 12 centered on an axis 14. The tubular structure 12 defines a passage 16 through the cannula 10. Surgical instruments are inserted into the body during surgery through the passage 16.

The tubular structure 12 comprises a first tubular portion 20 and a second tubular portion 40 attached to the first tubular portion. The first tubular portion 20 is preferably made of a length of stainless steel tubing, but could alternatively be made of another suitable material. The first tubular portion 20 has a proximal end 22 and a distal end 24. Parallel cylindrical inner and outer surfaces 26 and 28, respectively, extend between the ends 22, 24 of the first tubular portion 20. The inner surface 26 defines a first passage portion 30 of the passage 16 through the cannula 10. The first passage portion 30 has a diameter D1 that is preferably in the range from 10 mm to 30 mm.

The second tubular portion 40 of the tubular structure 12 is attached to the distal end 24 of the first tubular portion 20. The second tubular portion 40 is preferably made from stainless steel, but could alternatively be made from another suitable material.

As best seen in the rollout view of FIG. 4, the second tubular portion 40 comprises an arcuate segment 42 of sheet stock. The arcuate segment 42 includes first and second arcuate edges 44 and 46, respectively, and first and second planar edges 48 and 50, respectively. The first and second planar edges 48 and 50 are rolled in an overlapping manner to form the tubular configuration of the second tubular portion 40.

When the second tubular portion 40 has been rolled into its tubular configuration, the first and second arcuate edges 44 and 46 define oppositely disposed first and second ends 60 and 62 (FIGS. 1 and 2), respectively, of the second tubular portion. The first and second ends 60 and 62 are connected by a central portion 64. The first end 60 of the second tubular portion 40 is attached to the distal end 24 of the first tubular portion 20 by a single fastener, such as a rivet 66. The rivet 66 extends through two aligned apertures 68 (FIG. 4) at the first end 60 of the second tubular portion 40. The first end 60 of the second tubular portion 40 is pivotable about the rivet 66.

The second tubular portion 40 includes parallel inner and outer surfaces 70 and 72 (FIGS. 1 and 2), respectively, extending between the first and second ends 60 and 62. The inner surface 70 defines a second passage portion 74 of the passage 16 through the cannula 10 that extends as a continuation of the first passage portion 30 in the first tubular portion 20.

An arcuate slot 80 is formed in the second tubular portion 40 and extends between the inner and outer surfaces 70 and 72 of the second tubular portion. The arcuate slot 80 extends along a curvilinear path in the central portion 64 of the second tubular portion 40 toward the second end 60 of the second tubular portion. The arcuate slot 80 has a first terminal end 82 located in the central portion 64 of the second tubular portion 40. A second terminal end 84 of the arcuate slot 80 is located adjacent the intersection of the second arcuate edge 46 and the first planar edge 48 of the arcuate segment 42.

A guide pin 90 is attached to the inner surface 70 of the second tubular portion 40 adjacent the intersection of the second arcuate edge 46 and the second planar edge 50. In the tubular configuration of the second tubular portion 40, the guide pin 90 is located in the arcuate slot 80 and is movable along the curvilinear path of the arcuate slot. A washer 92 is secured an inner end of the guide pin 90 to retain the guide pin in the arcuate slot 80.

Figure 2:
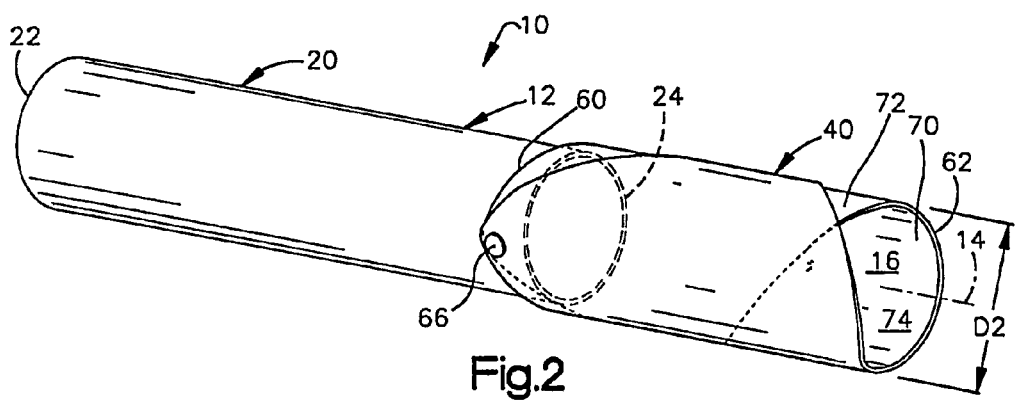
FIG. 2 is a perspective view of the cannula of FIG. 1 with parts removed for clarity, the cannula being shown in a contracted condition.
Figure 6:
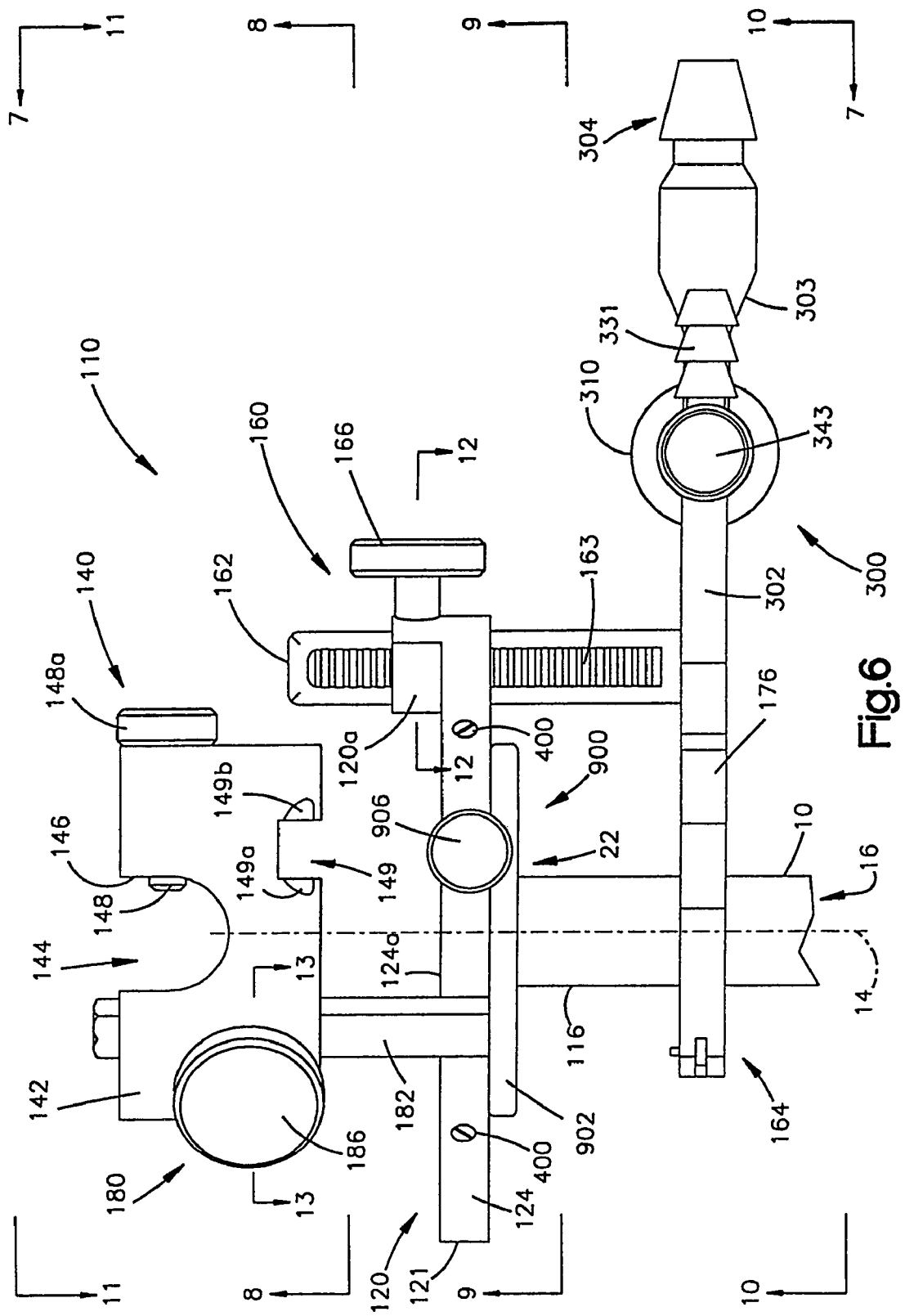
FIG. 6 is a schematic view of a support apparatus constructed for use with the present invention.
Figure 7:
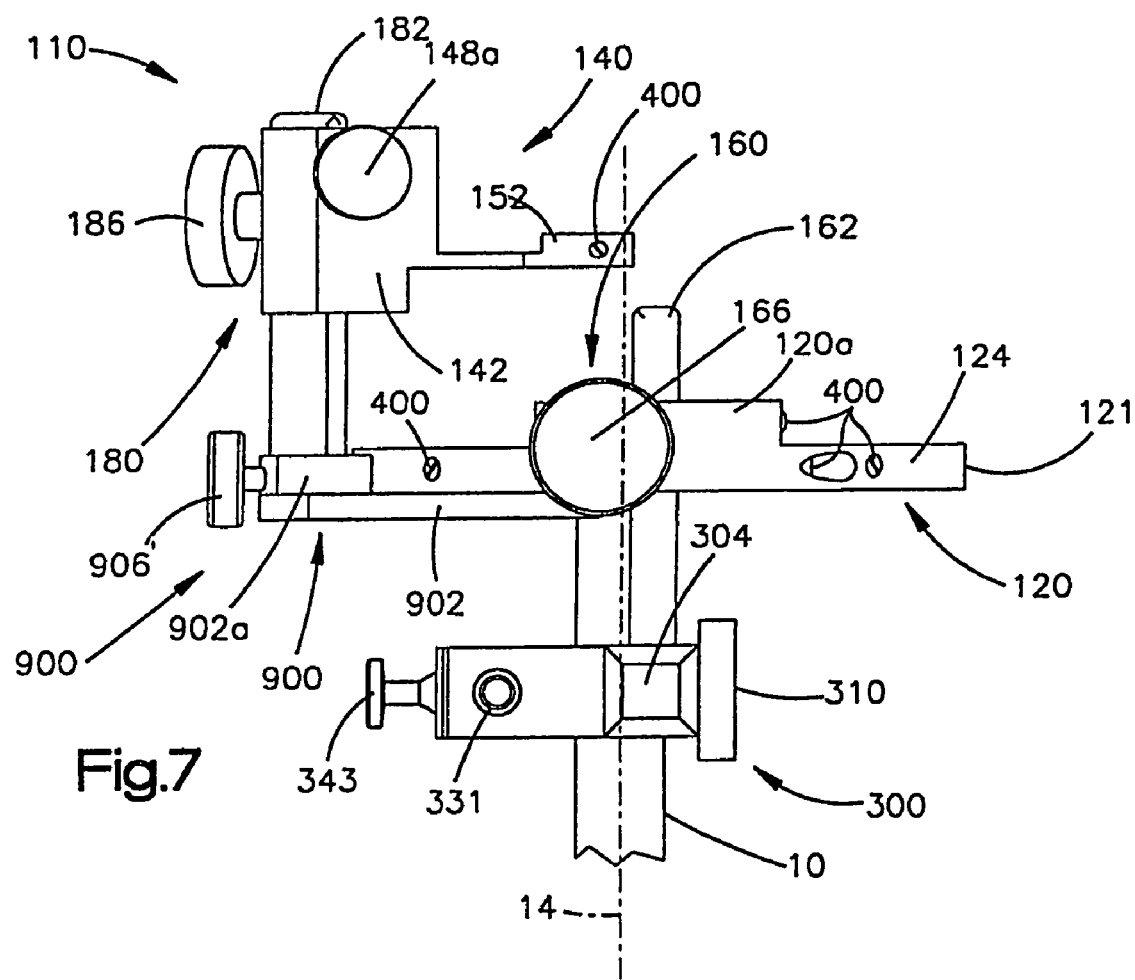
FIG. 7 is a schematic view taken along line 7-7 in FIG. 6.
Figure 8:
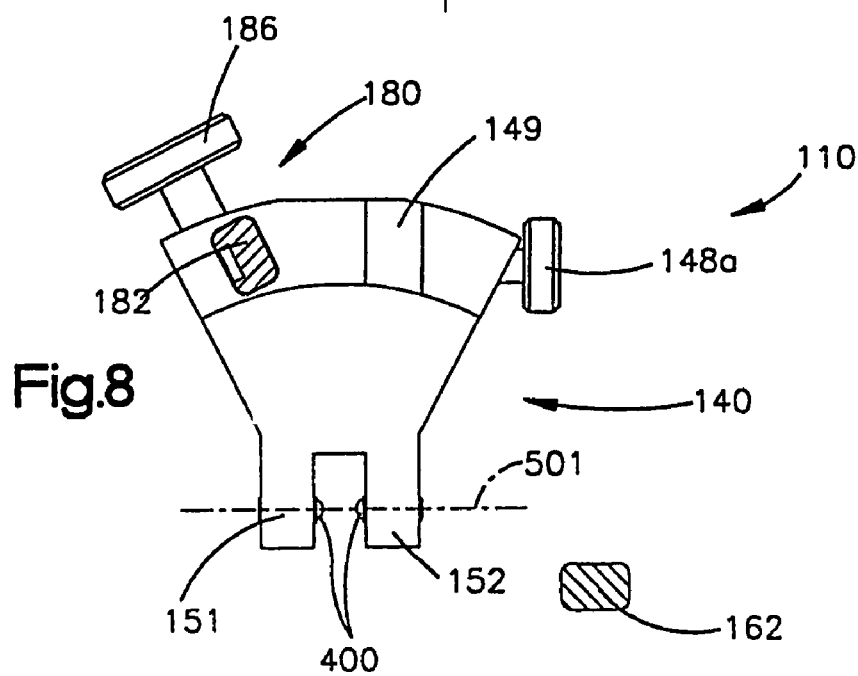
FIG. 8 is a schematic view taken along line 8-8 in FIG. 6 showing part of the support of FIG. 6.
Figure 11:
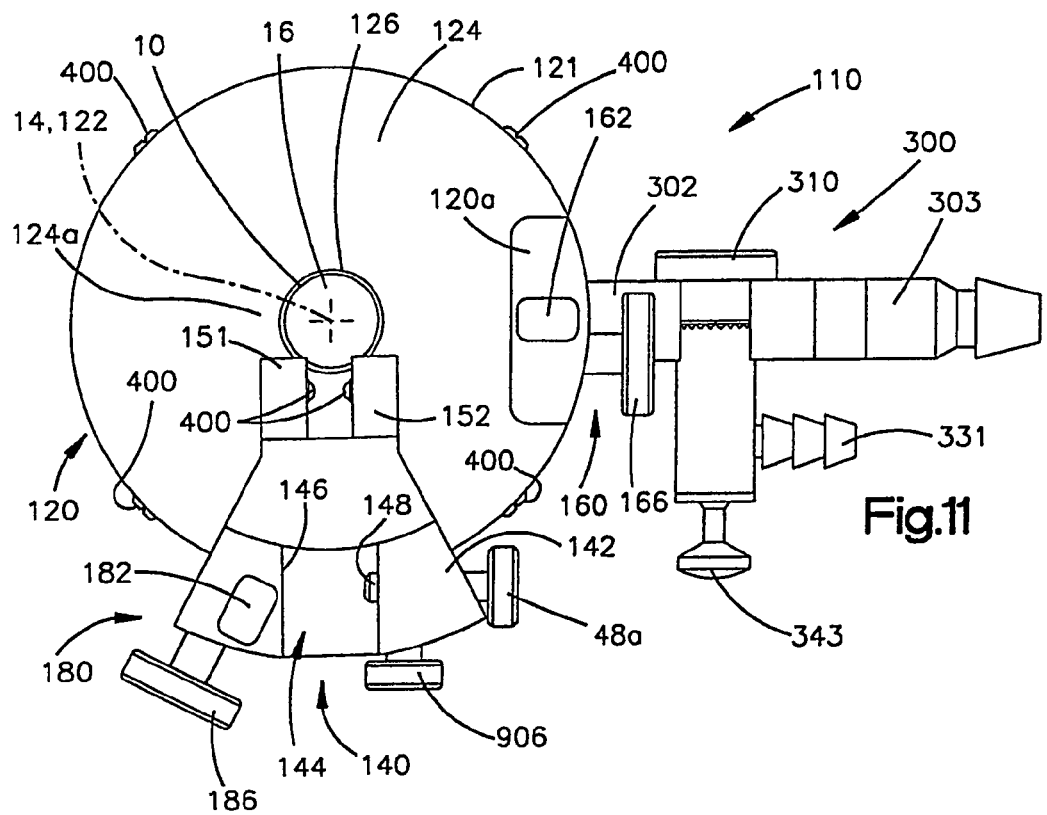
FIG. 11 is a schematic view taken along line 11-11 in FIG. 6.
Figure 14:
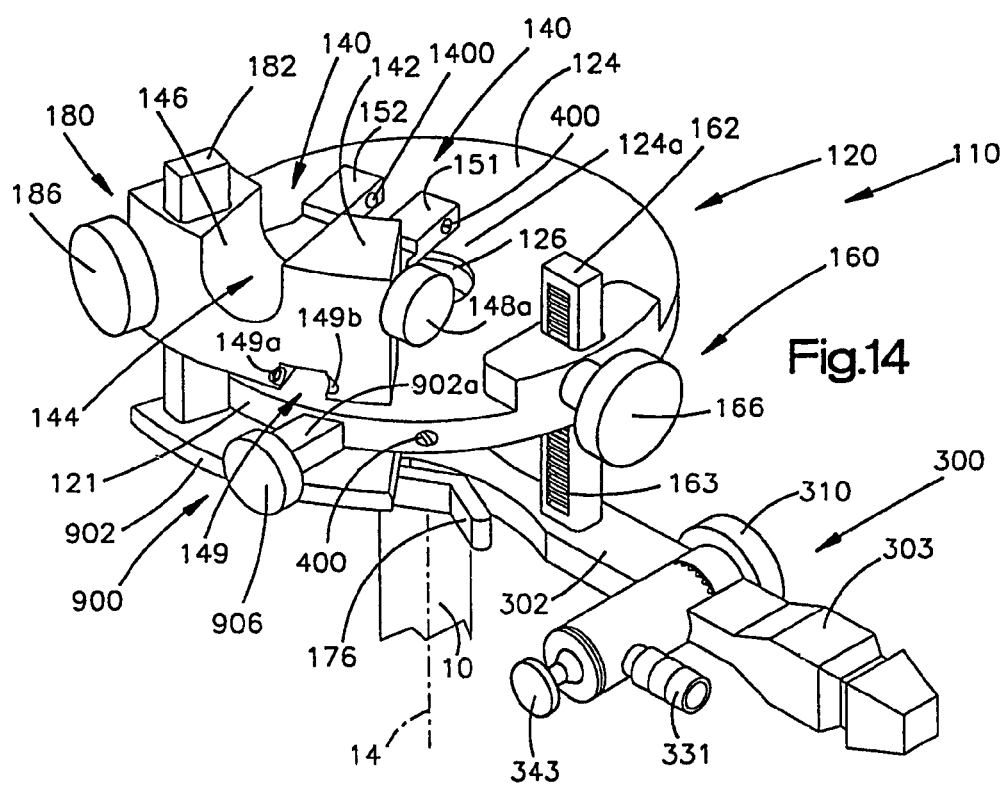
FIG. 14 is a perspective view of the support apparatus of FIG. 6.

The second tubular portion 40 of the tubular structure 12 is expandable from a contracted condition shown in FIG. 2 to an expanded condition shown in FIG. 1. In the contracted condition, the guide pin 90 is located in the first terminal end 82 of the arcuate slot 80 in the second tubular portion 40 and the second passage portion 74 defined by the second tubular portion is cylindrical in shape. The second passage 74 has a generally constant diameter D2 (FIGS. 2 and 3) that is approximately equal to the diameter D1 of the first tubular portion 20. Thus, the cross-sectional area of the second passage portion 74 at the second end 62 of the second tubular portion 40, which is function of the diameter D2, is approximately the same as the cross-sectional area at the first end 60 of the second tubular portion and is approximately the same as the cross-sectional area of the first passage portion 30 in the first tubular portion 20.

In the expanded condition, the guide pin 90 is located in the second terminal end 84 of the arcuate slot 80 in the second tubular portion 40 and the second tubular portion has a conical configuration. At the second end 62 of the second tubular portion 40, the second passage portion 74 has a diameter D3 (FIG. 3) that is larger then the diameter D2 of the second passage portion at the first end 60. Preferably, the diameter D3 of the second passage portion 74 at the second end 62 of the second tubular portion is 40% to 80% greater than the diameter D1 of the second passage portion at the first end 60. Thus, in the expanded condition, the cross-sectional area of the second passage portion 74 at the second end 62 of the second tubular portion 40, which is function of the diameter D3, is 16% to 64% greater than the cross-sectional area of the second passage portion at the first end 60 of the second tubular portion. In the expanded condition, the cross-sectional area of the second passage portion 74 at the second end 62 of the second tubular portion 40 is large enough to overlie a major portion of at least two adjacent vertebrae.

The cannula 10 includes an outer layer 100 (FIG. 1) for maintaining the second tubular portion 40 of the cannula in the contracted condition. It is contemplated that other suitable means for maintaining the second tubular portion 40 in the contracted condition could be employed. In accordance with a preferred embodiment of the present invention, the outer layer 100 comprises a section of plastic tubing 102 which is heat shrunk over both the first and second tubular portions 20 and 40 to hold the second tubular portion in the contracted condition.

In addition, a loop of polyester string 104 for tearing the heat shrunk tubing 102 is wrapped around the heat shrunk tubing so that it extends both underneath and on top of the tubing. An outer end 106 of the string 104 extends beyond the tubing 102.

FIG. 1 shows an actuatable device 111 for expanding the second tubular portion 40 from the contracted condition to the expanded condition. In accordance with a preferred embodiment of the present invention, the actuatable device 111 comprises a manually operated expansion tool 112. The expansion tool 112 resembles a common pair of scissors and has a pair of legs 114 pivotally connected to one another. The expansion tool 112 includes a frustoconical end section 116 formed by a pair of frustoconical halves 118. Each of the frustoconical halves 118 extends from a respective one of the legs 114 of the expansion tool 112. It is contemplated that other suitable means for expanding the second tubular portion 40 toward the expanded condition could be employed, such as an inflatable balloon (not shown).

During an endoscopic surgical procedure, the cannula 10 is inserted into the body of a patient in the contracted condition. The outer end 106 of the string 104 is then manually pulled on by the surgeon. Pulling on the string 104 tears the heat shrunk tubing 102 most of the way along the heat shrunk tubing, which frees the second tubular portion 40 for expansion. The heat shrunk tubing 102, in its torn condition, remains attached or secured to the first tubular portion 20.

Next, the expansion tool 112 is inserted into the passage 16 in the cannula 10 until the frustoconical end section 114 is located at the second end 62 of the second tubular portion 40. The legs 114 of the expansion tool 112 are manually separated, causing the frustoconical halves 118 to separate also. As the halves 118 separate, a radially outward directed force is exerted on the inner surface 70 of the second tubular portion 40 by the halves 118, causing the second tubular portion to expand toward the expanded condition. Under the force of the expanding expansion tool 112, the guide pin 90 slides from the first terminal end 82 of the arcuate slot 80 to the second terminal end 84 of the arcuate slot to permit the expansion of the second tubular portion 40. The expansion tool 112 can be rotated about the axis 14 to ensure that the second tubular portion 40 of the cannula 10 is completely expanded to the expanded condition. The expansion tool 112 is then collapsed and removed so that one or more surgical instruments (indicated schematically at 21 in FIG. 5) and a viewing element can be received through the cannula 10 and inserted into a patient's body 130. The expandable second tubular portion 40 of the cannula 10 provides a significantly larger working area for the surgeon inside the body 130 within the confines of the cannula.

The expanded tubular portion 40 can dilate and locally retract and separate spinalis muscle and soft tissues from the vertebrae thereby creating an endoscopic operating field at the surgical site. This endoscopic operating field within the spinal muscles differs from arthroscopic, laparoscopic, or cystoscopic working spaces in that there is no physiologic space or defined tissue plane that can be insufflated with air or distended with fluid.

FIGS. 6-23 illustrate one suitable support apparatus for use in a method in accordance with the present invention. The support apparatus 110 includes a first support 120, a second support 140, a first adjustment mechanism 160, a second adjustment mechanism 180, and a third adjustment mechanism 900.

As viewed in FIGS. 2 and 17, the first support 120 is associated with the cannula 10 and has a circular perimeter 121. The perimeter 121 has a center 122 located on the axis 14. The first support 120 comprises a circular platform, or disk 124, which has a circular opening 126 in the central area of the disk 124 for receiving the proximal end 22 of the cannula 10. The circular opening 126 has a center located on the axis 14. The proximal end 22 of the cannula 10 can be easily inserted into and removed from the opening. The disk 124 has a projection portion 120a, which is located adjacent the perimeter 121 of the disk 124. The disk 124 has an upper circular surface area 124a, which surrounds the opening 126.

As viewed in FIG. 10, the second support 140 supports a viewing device 200 including a camera head 201 and an endoscope 202 with a rod and lens assembly 203, herein referred to as a viewing element, extending down through the passage 16 of the cannula 10. The second support 140 includes a body 142 having an opening 144 through which the viewing device 200 extends and a clamp 146 for clamping the viewing device 200 to the body 142 in the opening 144. The clamp 146 includes a threaded set screw 148 for securing the viewing device 200 to the body 142. The set screw 148 has a manually rotatable knob 148a and a stem threaded into the body 142. When rotated, the screw 148 moves axially relative to the body 142 to clamp or release the viewing device 200 depending on the direction of rotation of the screw 148.

The body 142 of the second support 140 further includes two extension arms 151, 152 (FIG. 8) for supporting the endoscope 202. Each extension arm 151, 152 includes a threaded bore for receiving a resilient detent member, or ball plunger 400.

As viewed in FIGS. 17 and 18, a ball plunger 400 is illustrated at another location in the support apparatus 110. Each ball plunger 400, including those in the extension arms 151, 152, has an externally threaded tubular body 402 with a cylindrical cavity 404 located therein. The cavity 404 houses a projection 406 and a coiled spring 408. The projections 406 of the two ball plungers 400 of the extension arms 151, 152 are spherical detent members 420 in the form of balls (not shown). The spring 408 urges each projection 406 against a lip portion 409 of the body 402. The lip portion 409 is located at one end of the cavity 404. As shown in FIG. 18, the other ball plungers 400 of the apparatus 10 have projections 406 with hemispherical extensions 420 and shoulder portions 422.

As viewed in FIG. 15, the endoscope 202 has corresponding hemispherical recesses (not shown) for receiving the spherical detent members (balls) of the ball plungers 400 which are located in extension arms 151, 152. The springs 408 will compress in each ball plunger 400 in each extension arm 151, 152 and the spherical detent members will move inward of each cavity 404 and then spring back into the hemispherical recesses in the endoscope 202, as the endoscope 202 is inserted between the extension arms 151, 152. The entire viewing device 200 will thus be secured between the extension arms 151, 152, but may be removed by overcoming the force of the spherical detent members of each ball plunger 400 in the extension arms 151, 152.

The ball plunger 400 further includes a head portion 430 with a slot 432 for engaging a tool, such as a screwdriver. The ball plunger 400 may be threadedly adjusted within the threaded bore of either extension arm 151, 152 to alter the distance that the spherical detent member 420 projects away from the extension arms 151, 152 (toward each other). This distance, along with the stiffness of each spring 408, will determine the holding force by which the endoscope 202 is secured between the extension arms 151, 152.

The first adjustment mechanism 160 provides for relative axial adjustment of the cannula 10 and the first support 120 along the axis 14. The first adjustment mechanism 160 includes a first toothed rack member 162, a cannula gripper mechanism 164 fixedly connected to the first rack member 162, a first manually adjustable, rotatable knob 166 rotatably carried by the projection portion 120a of the first support 120, and a first gear member 165 (FIG. 12) rotatable by the first knob 166 and in meshing engagement with the teeth 163 of the first rack member 162. The first support 120 and, in particular, the projection portion 120a, rotatably carries the first gear member 165 (FIG. 12).

Figure 12:
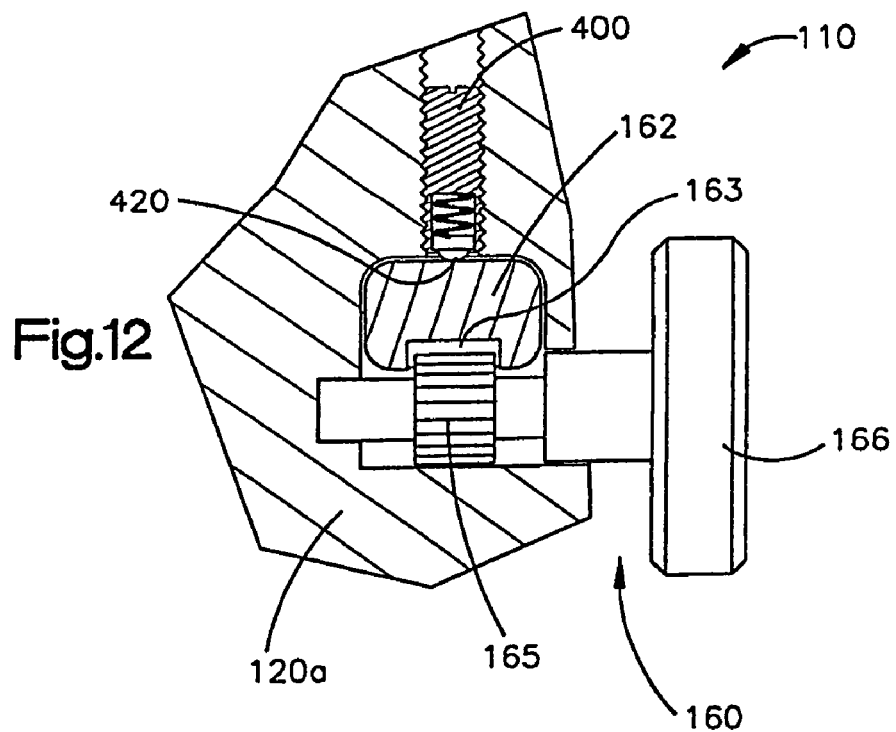
FIG. 12 is a schematic view taken along line 12-12 in FIG. 6 showing part of the support apparatus of FIG. 6.

The first rack member 162 is secured to slide axially within the first support 120 and the projection portion 120a by two ball plungers 400 (FIG. 12). One ball plunger 400 is tangentially threaded into a tapered, threaded bore (FIG. 7) in the perimeter 121 of the first support 120 and the other is tangentially threaded into a threaded bore in the projection portion 120a. The hemispherical extensions 420 thus frictionally engage a smooth portion (without teeth 163) of the first rack member 162 and bias the first rack member 162 against the first support 120 and the projection portion 120a. This biasing also maintains the engagement of the first rack member 162 and the first gear member 165 (FIG. 12).

As viewed in FIGS. 10 and 19, the cannula gripper mechanism 164 includes two gripper arms 172, 174 for clamping against the outer surface of the cannula 10, and a gripper actuating lever 176 for moving the arms 172, 174 into engagement with the outer surface of the cannula 10 and for releasing the arms 172, 174 from engagement with the cannula 10.

As viewed in FIG. 19, the cannula gripper mechanism 164 further includes a support pin 177, a coiled spring 188, a washer 189 with a bore (not shown), and a lock pin 190. The support pin 177 has a head 179, a shaft 180, and an oblong, or flat, end 181 that can mate with the bore in the washer 189. Other suitable structures could be used.

During assembly, the coiled spring 188 is interposed between the arms 172, 174. The flat end 181 of the support pin 177 is inserted through a circular bore in the first clamp arm 172, through the coil of the spring 188, through a circular bore in the second arm 174, and through the bore in the washer 189. The flat end 181 of the support pin 177 is then inserted into a slot 176a in the lever 176. The lock pin 190 is inserted through a bore in the lever 176 and through a bore in the flat end 181 of the support pin 177 thereby securing the mechanism 164 together and allowing the lever 176 to rotate about the lock pin 190. A camming surface 178 on the lever 176 adjacent the washer 189 forces the arms 172, 174 together to grip the cannula 10 as the lever 176 is rotated clockwise (as viewed in FIG. 10). Counterclockwise rotation of the lever 176 allows the spring 188 to force the arms 172, 174 apart and releases the cannula 10 from the gripper mechanism 164.

When the gripper mechanism 164 is either gripping the cannula 10 or released from the cannula 10 and the knob 166 is rotated, the disk 124 and parts attached to the disk 124 will move along the axis 14 of the cannula 10 relative to the cannula 10. After the support apparatus 110 is initially lined up with the cannula 10. The viewing device 200 may be positioned on the support apparatus 110 and adjusted along the axis 14 by rotation of knob 166.

The second adjustment mechanism 180 provides axial adjustment of the first and second supports 20, 40 relative to each other along the axis 14. The second adjustment mechanism 180 includes a second toothed rack member 182 connected to the first support 120, a second manually adjustable, rotatable knob 186 rotatably carried by the body 142 of the second support 140, and a second toothed gear member 185 (FIG. 13) rotatable by the second knob 186 and in meshing engagement with the teeth 183 of the second rack member 182. The second support 140, and in particular, the body 142, rotatably carries the second gear member 185 (FIG. 13).

The body 142 of the second support 140 may have a notch 149 which can fit around part 902a of the third adjustment mechanism 900 and allow the lower surface of the body 142 to completely abut the disk 124 as the body 142 is brought into an axial position adjacent the disk 124.

Figure 13:
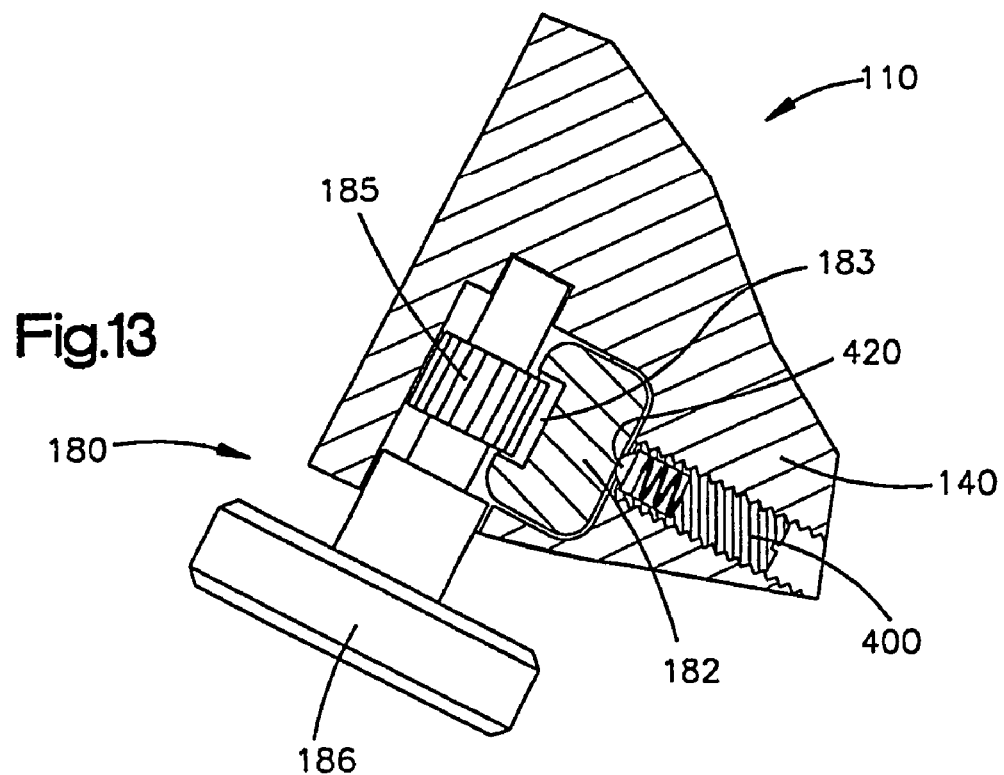
FIG. 13 is a schematic view taken along line 13-13 in FIG. 6 showing part of the support apparatus of FIG. 6.

The second rack member 182 is secured to slide axially within the second support 140 by a ball plunger 400 (FIG. 13). The ball plunger 400 is tangentially threaded into a threaded bore in the side of the notch 149 of the second support 140. The hemispherical extension 420 thus frictionally engages a smooth portion (without teeth 183) of the second rack member 182 and biases the second rack member 182 against the second support 140. The biasing also maintains the engagement of the second rack member 182 and the second gear member 185. Both sides of the notch 149 have tapered portions 149a, 149b for facilitating insertion of the ball plunger 400 into the threaded bore of the notch 149 of the second support 140. Rotation of the knob 186 causes the body 142 and the viewing device 200 attached thereto to move relative to the cannula 10 and disk 124 along the axis 14.

The third adjustment mechanism 900 provides arcuate, circumferential adjustment of the second support 140 about the axis 14 relative to the first support 120. The third adjustment mechanism 900 includes a wedge-shaped support member 902 (FIG. 9) fixedly connecting the second rack member 182 to a ring member 904 that is rotatably supported by the first support 120 and rotatable about the axis 14 relative to the first support 120 (FIG. 17).

The third adjustment mechanism 900 further includes a third manually adjustable, rotatable knob 906 that is part of a set screw. The set screw is rotatably threaded into a projection portion 902a of the support member 902 and is engageable with the circular perimeter 121 of the disk 124 of the first support 120 to lock the support member 902 in an arcuate position relative to the first support 120 and the axis 14.

As viewed in FIGS. 17 and 18, the ring member 904 is supported within a cylindrical, open ended recess 905 of the first support 120. The recess 905 is concentric about the axis 14. The perimeter 904a of the ring member 904 has a groove 904b for engaging a plurality of ball plungers 400 (preferably four equally spaced apart) in the first support 120. Each of these ball plungers 400 is similar in construction. Each ball plunger 400 is threaded radially into the perimeter 121 of the first support 120 to provide a hemispherical extension 420 extending into the recess 905 of the first support 120.

The ring member 904 thus is biasingly supported within the recess 905 of the first support 120 and can rotatably slide within the recess 905 about the axis 14. The ball plungers 400 operatively support the ring member 904 in the recess 905 of the first support 120. The ring member 904, along with the second support 140 and the second and third adjustment mechanisms 180, 900, can be easily removed from the recess 905 for cleaning, maintenance, etc. of the parts by overcoming the force applied by the ball plungers 400 to the ring member 904. When the knob 906 is rotated to disengage the perimeter 121 of disk 124, the body 142 and parts connected thereto can be manually rotated about the axis 14. This causes the viewing device 200 to rotate about the axis 14 of the cannula 10 and enables the surgeon to view different parts of the surgical sight as desired.

As viewed in FIG. 16, the fixed connections of the first rack member 162 to a support arm 300, the second rack member 182 to the wedge-shaped support member 902, and the support member 902 to the ring member 904 may be made by one or more suitable metal fasteners 290, such as rivets or bolts. The entire support apparatus 110 can be constructed from metal or any other suitable material having sufficient mechanical strength and durability. Certain parts may be made from materials permitting X-rays and other techniques for viewing the surgical sight (i.e., radiolucent parts). Other parts may also be made from non-magnetic materials to reduce electromagnetic interference (i.e., electromagnetic insulating parts).

As viewed in FIGS. 20-22, the gripper's arms 172, 174 are a part of the support arm 300 for attaching the support apparatus 110 to a mechanical robotic arm 301. The support arm 300 includes an arm portion 302 that is formed integrally with the arms 172, 174. The arms 172, 174 are integrally constructed with the arm portion 302.

The support arm 300 also includes an arm portion 303. The arm portion 303 has an attaching structure 304, including a groove 305, which snaps into a socket in the mechanical arm 301. Detents of any suitable type and designated 306 in the mechanical arm 301, hold the arm portion 303 in position in the socket in the mechanical arm 301. The detents 306 may be controlled by external actuation levers (not shown) on the mechanical arm 301 for manually releasing the arm portion 303 from the mechanical arm 301.

The arm portions 302 and 303 are pivotally connected to each other by a fastener 310. The fastener 310 extends through an opening 311 in the arm portion 302 and threads into a threaded opening 312 in the arm portion 303. When the fastener 310 is released, the arm portions 302, 303 may pivot relative to each other about a pivot axis 314. The pivot axis 314 is centered on the axis of the fastener 310 and the axis of the threaded opening 312. When the fastener 310 is tightly screwed into the threaded opening 312, the arm portions 302, 303 are secured together against pivoting movement. When the fastener is released, the arm portions 303, 302 may pivot relative to each other about the axis 314.

The end of the arm portion 302, which is adjacent to the arm portion 303, has a convex surface 350, which is curved about the axis 314. The arm portion 303 has a concave surface 351, which is also curved about the axis 314. The surfaces 350, 351 move concentrically relative to each other when the arm portions 303 and 302 pivot relatively about the axis 314.

The arm portion 303 has a set of teeth 320 which encircle the axis 314 and which project axially toward a set of teeth 321 on the arm portion 302. The teeth 321 project axially toward the teeth 320. The teeth 320 and the teeth 321 mesh with each other and provide a locking action so that the arm portions 302, 303 are positively locked against relative movement about axis 314 when the fastener 310 is tightly screwed into the opening 312. The teeth 320, 321 comprise a lock which blocks relative rotation of the arm portions 302, 303 about the axis 314. When the fastener 310 is loosened, the arm portions 302, 303 may be rotated relative to each other about the axis 314, and thus, the arm portions 302, 303 may pivot relative to each other to adjust the position of the support apparatus 110.

A cylindrical projection 325 is welded to the arm portion 303. Thus, the projection 325 and arm portion 303 are fixedly connected together. The projection 325 is centered on the axis 314 and contains a chamber 328.

As viewed in FIG. 22, the chamber 328 communicates with a fluid passage 329 in a male fluid connector 331. The male connector 331 attaches to a male connector 333 on the mechanical arm 301 by means of a flexible hose 392 so that the fluid passage 329 communicates with a fluid passage in the mechanical arm 301.

As viewed in FIG. 20, the chamber 328 is closed at its upper end by a cap 335. The cap 335 has an opening 336 centered on the axis 314. The opening 336 communicates with the chamber 328. A manually movable internal valve member 340 normally closes the opening and blocks the chamber 328 from communicating with the ambient air surrounding the support arm 300. The valve member 340 is connected to a stem 341, which is also centered on the axis 314. The stem 341 has a knob or button 343 on its end that may be manually depressed to move the stem 341 and valve member 340 downward into the chamber 328. When the stem 341 and valve member 340 are so moved, the chamber 328 is in communication with the ambient air surrounding the device due to the unblocking of the opening 336.

The mechanical arm 301 is a known device and is of the type generally disclosed in U.S. Pat. No. 4,863,133. The mechanical arm 301 is sold by Leonard Medical, Inc. 1464 Holcomb Road, Huntington Valley, Pa., 19006. The mechanical arm 301 includes relatively movable parts, which permit movement and adjustment of the support apparatus 110 in a variety in planes, directions, and orientations. The mechanical arm 301 permits easy movement when a vacuum is not applied to the arm 301. When a vacuum is applied to the arm 301, relative movement of the parts of the arm 301 is resisted, and therefore adjustment of the support apparatus 110 is difficult.

When the button 343 is depressed, the chamber 328 loses its vacuum and the pressure in the chamber 328 increases toward ambient pressure. The passage 329 communicates this pressure increase to the mechanical arm 301, and thus the parts of the mechanical arm 301 are free to move and allow for adjustment of the position of the support apparatus 110 by the surgeon.

Accordingly, when the surgeon uses the support apparatus 110, the support arm 300 is snapped into the socket of the mechanical arm 301 where it is held by the detent 306. The surgeon may then depress the button 343 and relatively move parts of the mechanical arm 301, as well as the support apparatus 110 into the position where the surgeon desires the support apparatus 110 to be. This position may be where the opening 126 in the disk 124 is aligned with the proximal end 16 of the cannula 10 that has been positioned in the patient's body with the distal end 24 of the cannula 10 being located in an incision in the body of the patient. The viewing device 200 may be mounted on the support apparatus 110, and the surgeon may make adjustments prior to and during the surgical procedure as desired, as described above.

Figure 23:
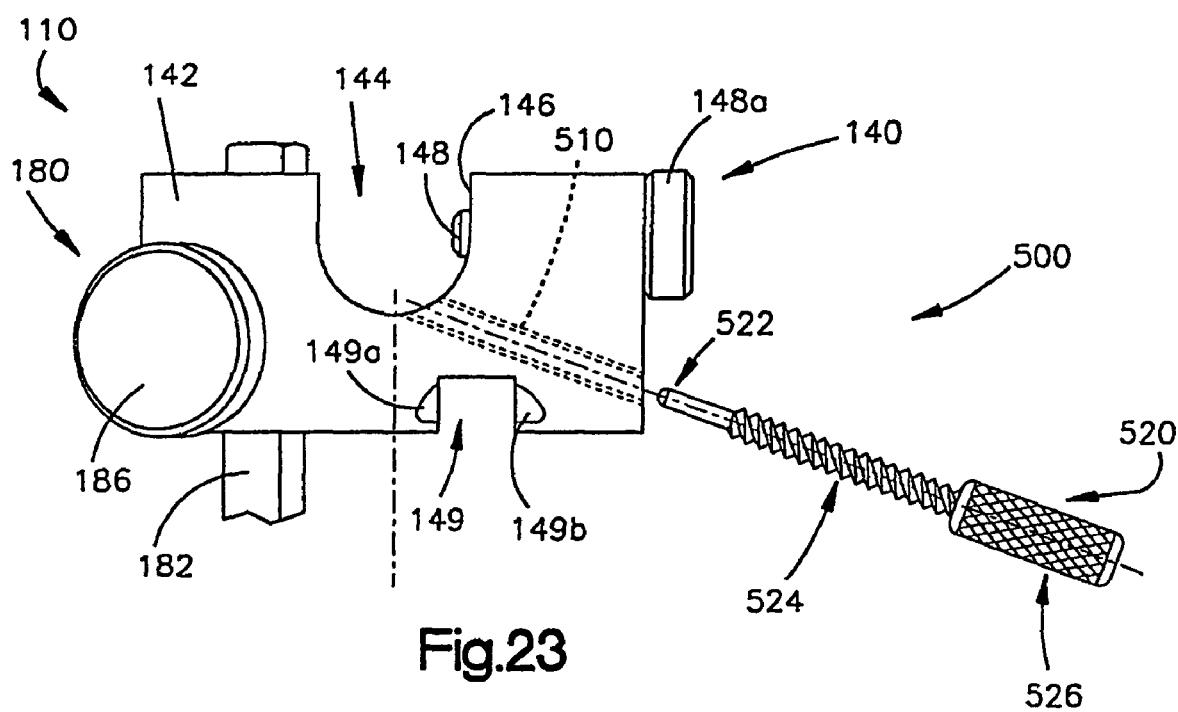
FIG. 23 is a schematic view of another feature of part of the support apparatus of FIG. 6.

As viewed in FIG. 23, the support apparatus 110 may include a second support with a fourth adjustment mechanism 500 for rotating the viewing device 200 about an axis 501 (FIG. 15) defined by the ball plungers 400 of the extension arms 151, 152 when set screw 148 is not clamping the viewing device 200 to the body 142. The axis 501 is offset from the axis 14 of the cannula 10 and perpendicular to the axis 14 of the cannula 10. Rotation of the viewing device 200 about axis 501 causes the endoscope 200 and the rod and lens assembly 203 to move perpendicular to the axis 14 of the cannula 10. This rotation will result in radial adjustment of the position of the rod and lens assembly 203 in a radial direction transverse to the axis 14.

The spring-loaded connections of the spherical detent members 420 of the ball plungers 400 and the hemispherical recesses of the endoscope 202 allow rotation about the axis 501 when the set screw 148 is released from clamping engagement of the viewing device 200.

The mechanism 500 includes a threaded bore 510 in the second support 140 and an adjustable member 520 for moving (vertically as viewed in the FIGS.) a part of the viewing device 200 about the axis 501. The adjustable member 520 has a rounded first end portion 522, a threaded middle portion 524, and a knurled second end portion 526, or knob. The bore 510 extends at an angle as shown in FIG. 23 from a lower portion of the second support 140 up to the opening 144 in the clamp 146 of the second support 140.

The adjustable member 520 is rotated and threaded into the bore 510 and may be rotated until the first end portion 522 protrudes into the opening 144 of the second support 140. Accordingly, when the surgeon wishes to adjust the rod and lens assembly 203 (within the surgical sight) about the axis 501 and radially relative to the axis 14 of the cannula 10, the surgeon may loosen the connection of the set screw 148 with the viewing device 200 and rotate the adjustable member 520 by manually rotating knob 526 so that the first end portion 522 vertically extends farther or less into the opening 144. This adjustment will adjust the part of the viewing device 200 engaged by the clamp 146 along the axis 14, rotate the viewing device 200 about the axis 501, and cause the lens 203 at the surgical site to move transverse to the axis 14 of the cannula 10. This will expand the area of the surgical site that the surgeon may view. When the adjustment is complete, the surgeon may tighten the set screw 148 and re-secure the viewing device 200 to the second support 140 of the support apparatus 110.

The method of securing two vertebrae 601, 602 together in accordance with the present invention may include the insertion of a vertebral fixation assembly 620 through the cannula 10 and attachment of the vertebral fixation assembly 620 to two vertebrae (such as the L4 and L5 vertebrae), as viewed in FIGS. 24-29. The fixation assembly 620 may be of any suitable construction and is shown in FIG. 26 as including four identical attachment devices 622. Each attachment device 622 includes a threaded fastener 624 or pedicle screw, placed in a vertebra 601 or 602, as viewed in FIGS. 25 & 28. The fastener 624, has a first threaded portion 626 with a first threaded diameter that threads into the vertebrae 601, 602 by screwing the fastener 624 into the vertebrae. The fastener 624 further includes a second threaded portion 628 with a second threaded diameter that may be less than the first threaded diameter. The second threaded portion 628 extends away from the vertebrae 601, 602.

A first hexagonal engagement surface 630, intermediate the first and second threaded portions 626, 628, allows gripping of the fastener 624 when the fastener is screwed into the vertebrae 601, 602. A first convex engagement surface 632, adjacent the first hexagonal engagement surface 630 and the second threaded portion 628, projects away from the vertebrae 601, 602. A second hexagonal engagement surface 634 projects away from the second threaded portion 628 and allows further gripping of the fastener 624.

Each attachment device 622 further includes a first fixation washer 640 (FIGS. 26 & 29) that engages the first convex engagement surface 632. The first fixation washer 640 includes a first concave engagement surface 642 for abutting and slidingly engaging the first convex engagement surface 632 of the fastener 624.

Figure 24:
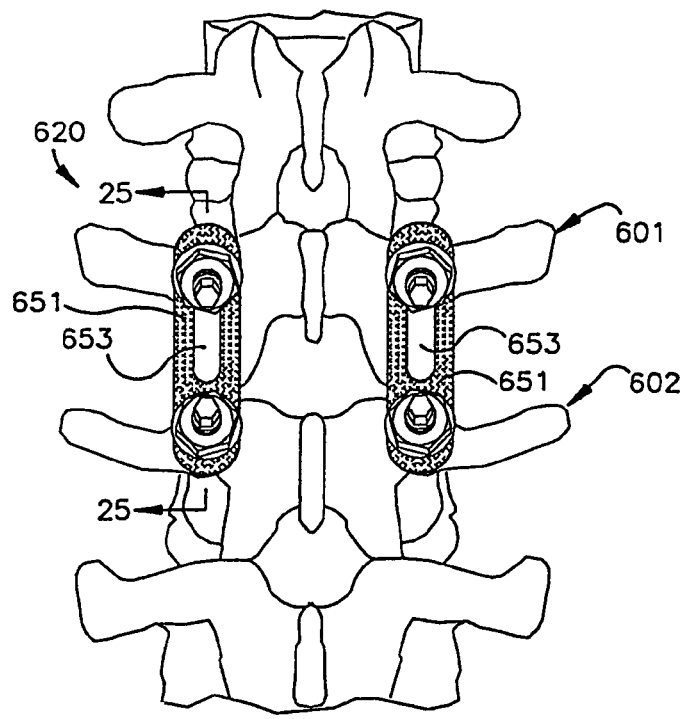
FIG. 24 is a schematic view of a fixation assembly attached to vertebrae of a patient.

The first fixation washer 640 further includes spikes 644, typically three, extending away from the vertebrae 601, 602. The spikes 644 of the first fixation washer 640 engage a lower knurled surface 652 of a vertebral fixation element 650 that in FIGS. 24-26 is a spine plate.

An upper knurled surface 654 of the fixation element 650 engages the spikes 664 of a second fixation washer 660 that is identical to the first fixation washer 640, but inverted, as viewed in FIGS. 26 & 29. A second convex engagement surface 672 of a threaded locking nut 670 abuts and slidingly engages the second concave engagement surface 662 of the second fixation washer 660 when the locking nut 670 is loosely threaded onto the second threaded portion 628 of the fastener 624.

Figure 25:
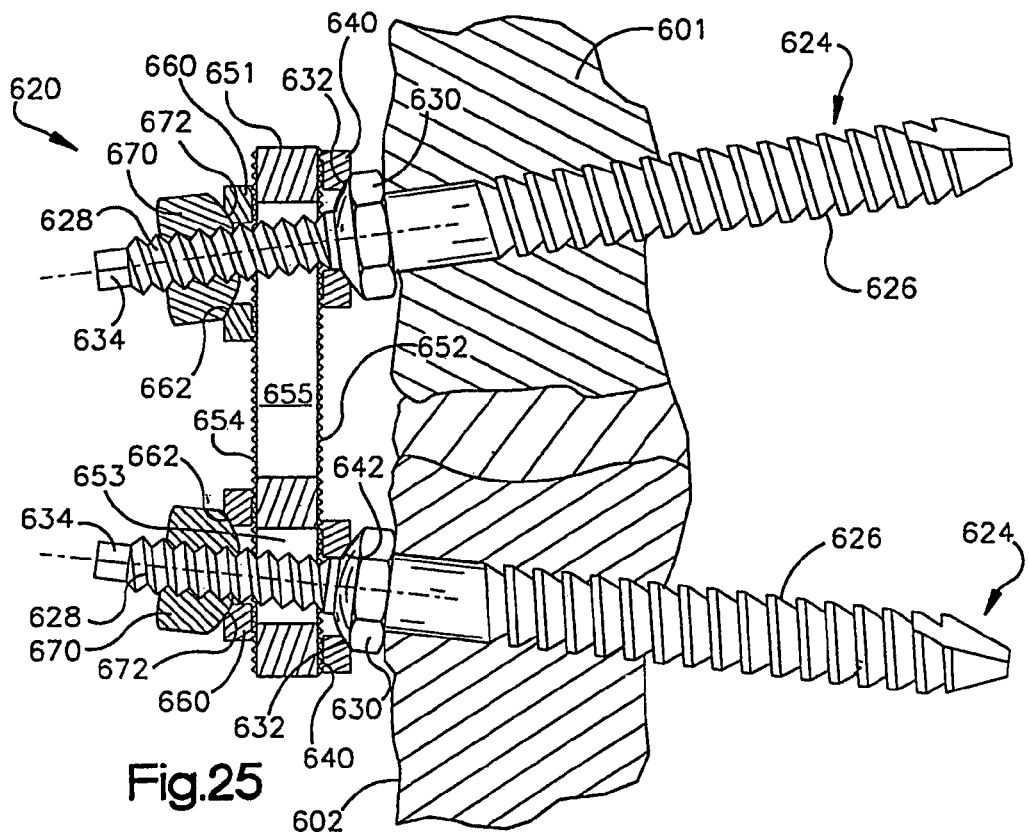
FIG. 25 is a schematic view taken along line 25-25 of FIG. 24.

The convex and concave engagement surfaces 632, 642, 662, 672 allow angular adjustment of the fixation elements 650, before the locking nut 670 is fully tightened, when the fasteners 624 are not threaded into the vertebrae 601, 602 exactly parallel to each other, as shown exaggerated in FIG. 25. These surfaces may typically allow for up to a 12-degree offset of the axes of the two fasteners 624.

One of two types of fixation elements 650 may typically be used to secure the vertebrae 601, 602 together. The first type may be a spinal plate 651 (FIG. 26) with two slots 653, 655 extending along the longitudinal axis 657 of the spinal plate. The second threaded portion 628 of one fastener 624, screwed into one vertebra 601, extends through one slot 653 and the second threaded portion 628 of another fastener 624, screwed into another vertebra 602, extends through the other larger slot 655. Two of the spinal plates 651, one on each side of the vertebrae 601, 602, are used to secure the two vertebrae together, as viewed in FIG. 24. The slots 653, 655 allow further transverse adjustment so that the same spinal plate 651 may be used for different size patients.

A second type of fixation element 650 may be two universal side blocks 651a (FIG. 29), each with one slot 653a extending along the longitudinal axis 657a of each side block and a securement opening 655a extending substantially perpendicularly to each slot 653a, as viewed in FIG. 29. The second threaded portion 628 of a fastener 624, screwed into one vertebra 601, extends through one slot 653a and the second threaded portion 628 of another fastener 624, screwed into another vertebrae 602, extends through a slot 653a in an identical side block 651a. The side blocks 651a further include lower and upper knurled surfaces 652a, 654a similar to the knurled surfaces 652, 654 of the spinal plate 651.

This second type of fixation element 650 further includes a rod 658a extending from the opening 655a in one side block 651a to the opening 655a in the other side block 651a. Set screws 659a secure the rod 658a in each opening 655a when the rod 658a is positioned properly to secure the vertebrae 601, 602 together, as viewed in FIG. 27.

Four of the side blocks 651a, one on each side of each vertebra 601, 602, and two rods 658a are used to secure the two vertebrae together. The slots 653a allow further transverse adjustment so that the same side block 651a may be used for different size patients. The rods 658a may also be cut to fit different sized patients.

The cannula 10, support apparatus 110, and vertebral fixation assembly 620 described above may be used to perform an operation which secures two vertebrae 601, 602 together, such as the posterolateral fusion and screw placement described above. This type of operation traditionally results in much blood loss because of the open access to the spine required for its performance. Utilizing the cannula 10 and support apparatus 110 for placement of the fixation assembly 620 at the surgical site and attachment of the fixation assembly 620 to the vertebrae 601, 602 in a manner to be described results in a much less invasive procedure and significantly less blood loss.

In accordance with the present invention, a method of fixing the vertebrae 601, 602 of a patient together at two surgical sites includes two main procedures. The first procedure includes the following steps: inserting a first cannula 10 into the body 130 of the patient adjacent one side of the spinal column; inserting a second cannula 10 into the body 130 of the patient adjacent the other side of the spinal column; expanding the second tubular portions 40 of both cannulae as described above thereby creating a substantially complete view of both sides of the two adjacent vertebrae 601, 602 utilizing two endoscopes 200 and one or more monitors.

Alternatively, instead of using two cannulae and two endoscopes simultaneously so that both sides of adjacent vertebrae may be worked on by the surgeon at the same time, only one side of the adjacent vertebrae may be worked on and then the other side of the adjacent vertebrae may be worked on. In this case, only one endoscope, one endoscope support 110, and one monitor is required. Two cannulae would most probably be used, one for each side of the vertebrae.

The second procedure includes accessing the vertebrae 601, 602 through the cannulae 10; drilling four insertion openings, one in each side of each vertebra 601, 602 utilizing suitable instruments extending through the cannula 10; inserting fasteners 624 through each cannulae and screwing one fastener into each insertion opening thereby securing each fastener 624 to a vertebra; checking the position of the vertebrae to ensure that the vertebrae have maintained the proper position and, if necessary, repositioning the vertebrae; moving eight fixation washers 640, 660, four locking nuts 670, and two fixation elements 650 through the cannulae; placing four fixation washers 640 and the fixation elements on the fasteners, each fastener extending through one fixation washer and one slot in each fixation element; placing the additional fixation washers 660 on the fasteners; and threading the locking nuts onto each fastener thereby fixing the fixation elements to the vertebrae and securing the vertebrae together in a natural and permanent position within the body. Also, bone graft may be moved through the cannula 10 and placed in and around the fixation element 650 and fasteners 624 to permit a posterior fusion across the bony elements of the vertebrae 601, 602.

If necessary, the disk between the vertebrae 601, 602 may be removed through the cannula; the area between the vertebrae cleaned and the vertebrae prepared for receiving a fusion cage or cages and/or disk replacement material. This would be done before inserting the fasteners 624 or attaching the fixation elements 650. The method may also include inserting, through the cannulae 10, one or more appropriately sized fusion cages and positioning the fusion cage(s) appropriately relative to the vertebrae 601, 602; and inserting bone graft tissue through the cannulae 10 and positioning the tissue in and around the fusion cage(s).

The fusion cage may be of any known construction. One typical fusion cage is a hollow rectangular cage that is inserted into grooves that are formed in facing bone surfaces of the vertebrae. Another type of fusion cage is a hollow cylindrical threaded cage which screws into position between the vertebrae. Any suitable fusion cage may be used.

The cannulae 10 and the shrink wrap 102 are then removed from the body and the incisions are suitably closed. After a time, vertebrae 601, 602 and bone graft will grow together across the fusion cage(s) and in and around the fixation elements 650. The vertebrae 601, 602 will then no longer require the fixation assembly to maintain their position. The fixation elements 650 and fasteners 624 may then be removed. The removal procedure may utilize the same type of apparatus as was used in the first and second procedures (i.e., cannula, support apparatus, etc.).

The first and second cannulae 10 may be shifted slightly in the incisions in the body 130 to desired locations within the incisions at any time during the first and second procedures or the removal procedure. This is accomplished by changing the position of the support apparatus 110 by manipulating the arm 301.

The method described above may, and most probably does, involve removal of tissue from the surgical site through the cannula 10. Muscle, fat, and bone may be removed through the cannula 10 to provide a proper view of the vertebrae 601, 602 and the location to receive the fixation assembly 620. Different tools may be used in the process of removing tissue. These tools may include a burr and/or tissue cutting blades that are inserted through the cannula 10.

A preferred tissue cutting blade device 710 is shown in FIGS. 30-31. The device 710 has an axis 712 and includes inner and outer cutting tubes 740, 750. Each of the inner and outer tubes 740, 750 has openings 741, 751 into their interiors. Cutting teeth 745, 755 are located on opposite sides of each opening 741, 751.

The inner tube 740 rotates about the axis 712 relative to the outer tube 750 within the outer tube. The inner tube 740 rotates in opposite directions a predetermined amount equal to one or more revolutions about the axis 712, then rotates in the opposite direction the same predetermined amount. Thus, the inner tube 740 oscillates about the axis 712. As the inner tube 740 oscillates/rotates about the axis 712, the cutting teeth 745, 755 on the inner and outer tubes 740, 750 cut tissue. Alternatively, the inner tube 740 may rotate in one direction (clockwise or counterclockwise) within the outer tube.

During the cutting of tissue, a saline solution or the like may be forced through the annular space 770 between the inner tube 740 and the outer tube 750 to the surgical site. Suction may be applied in the opening 741 of the inner tube 740 to remove the cut tissue and the saline solution from the surgical site.

A tubular sheath 760 receives the inner and outer cutting tubes 740, 750. The sheath 760 extends along the length of the cutting tubes 740, 750 and adjacent a distal end of the cutting tubes where the cutting teeth 745, 755 are located. The sheath 760 is a stainless steel tube that is electrically insulated along its length from the patient's body and from the outer tube 750. An electrical insulator 763, such as a suitable polymer coating, is provided over the outside and inside surfaces of the sheath 760. However, a selected area 762 of the outside surface of the sheath 760 adjacent the distal end of the cutting tubes 740, 750 is not coated with the insulator 763. A portion 765 of the distal end of the sheath 760 is cut away so that the cutting teeth 745, 755 on the cutting tubes 740, 750 are not blocked by the sheath 760 from cutting tissue.

An electric current from a current source 766 is applied to the sheath 760. The electric current flows through the sheath 760 and to the selected uncoated area 762 of the sheath. The current then flows through tissue and blood into the distal end of the outer cutting tube 750 and back to the current source through the outer cutting tube to form a completed circuit.

The current flow through the electrically energized sheath 760 and outer cutting tube 750 serves to electrocoagulate blood in the cutting area at the surgical site. Electrocoagulation of blood is known and any other suitable electrocoagulation device may alternatively be used.

From the above description, one skilled in the art should realize that viewing of the surgical site may be performed without using an endoscope. A microscope or glasses that magnify the site may be used. In fact, any suitable viewing device may be used. Also, the procedure discussed above mentions drilling the vertebrae. Any suitable alternative to drilling may be used such as using an awl or other instrument to form an opening to receive a fastener.

Also, from the above description of the invention, those skilled in the art will perceive improvements, changes and modifications. Such improvements, changes and modifications within the skill of the art are intended to be covered by the appended claims.

Having described the invention, the following is claimed:

1. A system enabling minimally invasive procedures at a surgical location at or near the spine of a patient, said system comprising:

an elongate body having an inner surface defining a passage extending through the elongate body and through which surgical instruments can be inserted to the surgical location, said elongate body capable of having a configuration when inserted within the patient wherein the cross-sectional area of said passage at a first location is greater than the cross-sectional area of said passage at a second location, wherein the first location is distal to the second location, said elongate body having a proximal portion and a distal portion, wherein the proximal portion is independently pivotable relative to the distal portion; and a support arm configured to support the proximal portion of the elongate body hands-free outside the patient when the distal portion is inserted at the surgical location, the support arm configured to pivot the proximal portion relative to the distal portion, and to support and maintain the proximal portion in the pivoted position.

2. The system of claim 1, wherein the support arm is operably connected to the proximal portion of the elongate body.

3. The system of claim 2, wherein the elongate body is arranged along an axis and the support arm is configured to substantially surround the axis when the elongate body is received by the support arm.

4. The system of claim 1, wherein the support arm comprises an arcuate portion at least partially surrounding a proximal portion of the elongate body.

5. The system of claim 4, wherein the arcuate portion extends more than 180 degrees around the proximal portion of the elongate body.

6. The system of claim 4, wherein the support arm has at least one adjustment mechanism configured to move the elongate body relative to the support arm.

7. The system of claim 4, wherein the elongate body is arranged along an axis and the arcuate portion of the support arm is substantially centered on the axis when the elongate body is received by the support arm.

8. The system of claim 1, further comprising a viewing device support.

9. The system of claim 8, wherein the viewing device support is coupled with the support arm.

10. The system of claim 8, further comprising a viewing device.

11. The system of claim 10, wherein the viewing device is selected from the group consisting of a camera, an endoscope, a microscope, and magnifying glasses.

12. The system of claim 1, wherein the support arm is configured to support the elongate body and to support an additional device relative to the passage of the elongate body, wherein the support arm extends generally perpendicular to a longitudinal axis of the elongate body when the support arm engages the elongate body.

13. The system of claim 12, wherein the support arm is configured to support the elongate body proximal of the first location.

14. The system of claim 12, wherein said additional device is a viewing device, the system further including the viewing device coupled to the support arm.

15. The system of claim 14, further including an adjustment mechanism configured to move the viewing device relative to the elongate body.

16. The system of claim 15, wherein the support arm is configured to indirectly support the viewing device.

17. The system of claim 15, wherein the adjustment mechanism adjustably moves the viewing device along an axis that is generally parallel to a longitudinal axis of the elongate body.

18. The system of claim 14, wherein the viewing device comprises a viewing element, wherein the viewing element includes one or more of a camera, an endoscope, a microscope, and magnifying glasses.

19. The system of claim 18, wherein the viewing element is configured to be extended through the passage toward the surgical location at or near the spine.

20. The system of claim 14, wherein the viewing device is configured to be extended through the passage toward the surgical location at or near the spine.

21. The system of claim 12, further comprising a viewing device operably coupled with the elongate body.

22. The system of claim 21, wherein the viewing device is adjustable along an axis that is generally parallel to a longitudinal axis of the elongate body.

23. The system of claim 21, wherein the viewing device comprises a viewing element, wherein the viewing element includes one or more of a camera, an endoscope, a microscope, and magnifying glasses.

24. The system of claim 23, wherein the viewing element is configured to be extended through the passage toward the surgical location at or near the spine.

25. The system of claim 1, wherein the support arm is configured to removably receive the proximal end of the elongate body.

26. A device for providing access to a first location adjacent the spine of a patient, comprising:

an elongate body having a tubular proximal end and a distal end and a passage extending through the elongate body through which surgical instruments can be delivered, said elongate body being enlargeable such that the passage at a distal location is larger than the passage at a proximal location; and a support arm operably connected to the proximal end of the elongate body, the support arm extending generally transverse to an axis defined along the passage of the elongate body between the proximal and distal ends, the support arm configured to support and position the elongate body outside of the patient when the device is applied to the patient, the support arm configured such that a user may place the elongate body in a desired position relative to the patient, and the support arm maintains the elongate body in the desired position without being held by a user.

27. The device of claim 26, wherein the elongate body is configured with an amount of overlap, the amount of overlap being reduced when the elongate body is enlarged.

28. The device of claim 26, wherein the elongate body has a length extending between the first location and the skin of the patient when the device is applied to the patient.

29. A system enabling minimally invasive procedures at a surgical location at or near the spine of a patient, said system comprising:

an elongate body having an inner surface defining a passage extending through the elongate body and through which surgical instruments can be inserted to the surgical location, said elongate body being expandable from a first configuration for insertion into a patient to a second configuration when inserted within the patient wherein the cross-sectional area of said passage at a first location is greater than the cross-sectional area of said passage at a second location, wherein the first location is distal to the second location; and a first support arm configured to support the elongate body outside the patient when the system is applied to the patient the support arm configured to move the elongate body and to maintain the elongate body in a desired position relative to the patient without being held by a user; and a second support arm configured to support a viewing device without being held by a user, the second support arm coupled to the first support arm.

30. The system of claim 29, wherein the elongate body extends along an axis and the first support arm is configured to substantially surround the axis when the elongate body is received by the first support arm.

31. The system of claim 30, further comprising an adjustment mechanism configured to provide axial adjustment of the first and second support arms relative to each other along the axis.

32. The system of claim 31, wherein the second support arm is configured to position the viewing device in the passage.

33. The system of claim 31, further comprising a viewing device selected from the group consisting of a camera, an endoscope, a microscope, and magnifying glasses.

34. The system of claim 29, wherein the first support arm comprises an arcuate portion at least partially surrounding a proximal portion of the elongate body.

35. The system of claim 34, wherein the arcuate portion extends more than 180 degrees around the proximal portion of the elongate body.

* * * * *